United States Patent
Zheng et al.

(10) Patent No.: US 7,612,080 B2
(45) Date of Patent: Nov. 3, 2009

(54) GTPASE INHIBITORS AND USE THEREOF FOR CONTROLLING PLATELET HYPERACTIVITY

(75) Inventors: Yi Zheng, Cincinnati, OH (US); Huzoor Akbar, Athens, OH (US); David A. Williams, Cincinnati, OH (US); Wieslaw Adam Mazur, Mason, OH (US)

(73) Assignee: Cincinnati Children's Hospital Medical Center, Cincinnati, OH (US)

( * ) Notice: Subject to any disclaimer, the term of this patent is extended or adjusted under 35 U.S.C. 154(b) by 426 days.

(21) Appl. No.: 11/283,556

(22) Filed: Nov. 18, 2005

(65) Prior Publication Data

US 2006/0135542 A1     Jun. 22, 2006

Related U.S. Application Data

(60) Provisional application No. 60/629,380, filed on Nov. 19, 2004.

(51) Int. Cl.
*A61K 31/506* (2006.01)
(52) U.S. Cl. .................................................... 514/275
(58) Field of Classification Search .................. None
See application file for complete search history.

(56) References Cited

U.S. PATENT DOCUMENTS

| | | | |
|---|---|---|---|
| 6,197,771 | B1 | 3/2001 | Bigge et al. |
| 6,617,359 | B2 | 9/2003 | Wohlfart et al. |
| 2004/0137518 | A1 | 7/2004 | Lambert et al. |

FOREIGN PATENT DOCUMENTS

WO    WO 2004/076445      9/2004

OTHER PUBLICATIONS

Kawano et al., Nagoya J. Med. Sci, vol. 65, pp. 1-8, 2002.*
Etienne-Manneville, S. et al., "Rho GTPases in Cell Biology," Nature, vol. 420, 629-635, Dec. 2002.
Etienne-Manneville, S. et al., "Rho GTPases in. Cell Biology," Nature, vol. 420, 629-635, Dec. 2002.
Fiegen, et al., "Alternative splicing of Rac1 generates Rac1b, a self-activating GTPase," J. Biol. Chem., vol. 279, No. 6, pp. 4743-4749, (Feb. 6, 2004).
Flower, et al., "Drug design, cutting edge approaches," Royal Society of Chemistry, Cambridge, UK, pp. 21-27, ISBN 0-085404-816-2, (2002).
Grizot, et al., "Crystal structure of the Rac1-RhoGDI complex involved in NADPH oxidase activation," Biochemistry, vol. 40, pp. 10007-10013, (2001).
File History for U.S. Appl. No. 10/994,165, filed Nov. 19, 2004, for the period of Jun. 4, 2008-Oct. 16, 2008.
File History for U.S. Appl. No. 11/496,959, filed Jul. 31, 2006, for the period of Jun. 4, 2008-Oct. 16, 2008.

* cited by examiner

*Primary Examiner*—Brian-Yong S Kwon
(74) *Attorney, Agent, or Firm*—Knobbe Martens Olson & Bear LLP

(57) ABSTRACT

The preferred embodiments generally relate to methods and compositions that affect the GTP-binding activity of members of the Rho family GTPases, preferably Rac (Rac1, Rac2 and/or Rac3), such compositions include compounds that modulate the GTP/GDP exchange activity, along with uses for the compounds including screening for compounds which recognize Rac GTPase, and methods of treating pathological conditions associated or related to a Rho family GTPase, including Rac. The preferred embodiments also relate to methods of using such compounds, or derivatives thereof, e.g., in therapeutics, diagnostics, and as research tools.

9 Claims, 15 Drawing Sheets

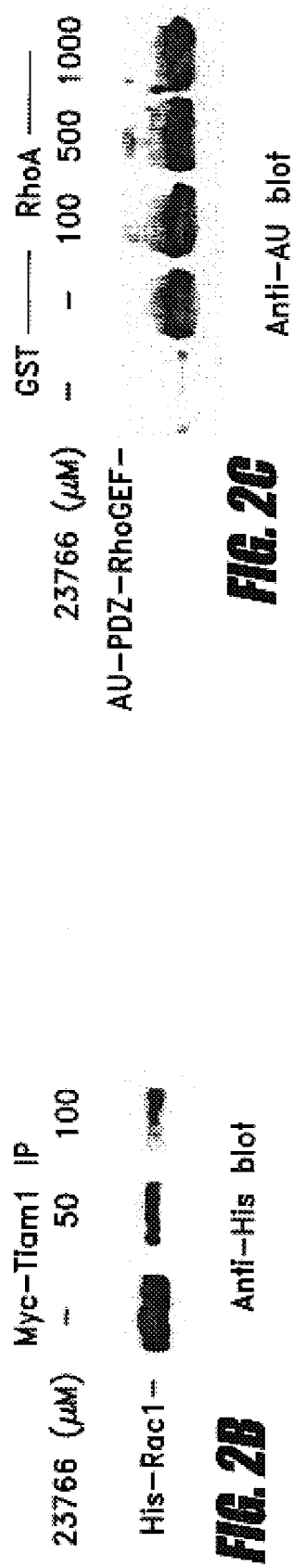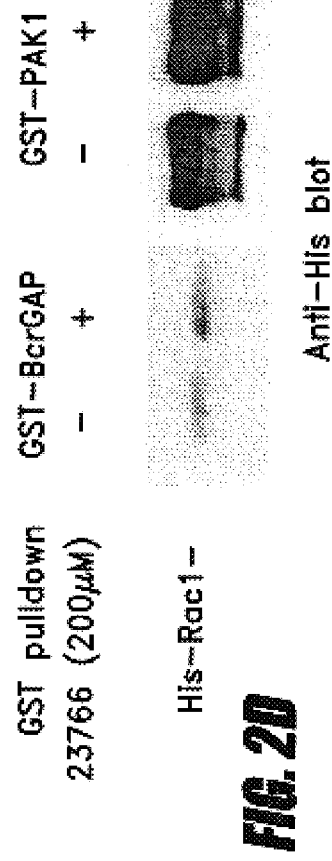
FIG. 2C
FIG. 2B
FIG. 2D

Tiam1+ 23766    0 μM    100 μM

Tiam1+ 0 μM

Tiam1+ 100 μM

PC-3                    PC-3 + 25 μM 23766

GTPASE INHIBITORS AND USE THEREOF FOR CONTROLLING PLATELET HYPERACTIVITY

CROSS REFERENCE TO RELATED APPLICATIONS

This patent application claims priority under 35 U.S.C. 119(e) to U.S. Provisional Patent No. 60/629,380, filed Nov. 19, 2004, which is incorporated herein by reference in its entirety. This patent application also claims priority to International Patent Application No. PCT/US2005/041949, filed Nov. 18, 2005.

STATEMENT REGARDING FEDERALLY SPONSORED RESEARCH

This invention was made in part with Government support under Grant No. R01 GM60523 and No. R01 GM53943 awarded by the National Institutes of Health. The Government can have certain rights in this invention.

BACKGROUND OF THE INVENTION

1. Field of the Invention

The present invention generally relates to methods and compositions that affect the GTP-binding activity of members of the Ras superfamily GTPases, along with uses for the compounds including methods of treating pathological conditions associated or related to a Ras superfamily GTPase.

2. Description of the Related Art

Rho family GTPases are molecular switches that control signaling pathways regulating cytoskeleton reorganization, gene expression, cell cycle progression, cell survival, and other cellular processes (Etienne-Manneville, 2002), which is incorporated herein by reference in its entirety.

Rho family proteins constitute one of three major branches of the Ras superfamily. Rho proteins share approximately 30 percent amino acid identity with the Ras proteins. At least 14 mammalian Rho family proteins have been identified thus far, including RhoA, RhoB, RhoC, RhoD, RhoE/Rnd3, Rnd1/Rho6, Rnd2/Rho7, RhoG, Rac1, Rac2, Rac3, Cdc42, TC10, and TTF.

Clinical trials have shown that antiplatelet therapy may significantly improve the care of patients with cardiovascular disease and stroke by blocking platelet deposition on the surface of damaged blood vessels. Aspirin, the most commonly used antiplatelet agent has limited usefulness because of the side effect of gastrointestinal bleeding and the fact that up to one-third of patients on chronic aspirin therapy develops aspirin resistance. Aspirin's irreversible effect on platelet function and long duration of action add to the inherent risk of bleeding associated with use of this drug. The thienopyridine derivative, clopidogrel has shown some effectiveness in the prevention of vascular events, but may have similar potential for severe side effects, such as thrombotic thrombocytopenic purpura, as the related drug ticlopidine. There has been very little experience with the thienopyridine derivative drugs in children. The more powerful parenterally-administered glycoprotein IIb/IIIa inhibitors abciximab, tirofibran and eptifibatide have had limited usefulness except in short-term clinical trials in conjunction with percutaneous interventional vascular repair and stenting in adults.

SUMMARY OF THE INVENTION

Therefore there is an urgent need for novel antiplatelet agents with alternative mechanisms of action, that can be orally administered, preferably with a short duration of action for use in the prevention of arterial thrombosis including stroke and cardiovascular disease (such as Kawasaki syndrome and moyamoya) in children.

The preferred embodiments provide compounds that are potent and selective inhibitors of Rho GTPases. Specifically, these compounds can be used to inhibit Rho-related Rac GTPase. These inhibitors can be used to treat diseases associated with Rac disregulation, including platelet hyperreactivity.

A preferred embodiment provides a method for treating platelet hyperreactivity, comprising administering to a subject an effective amount of at least one compound having the formula (IIa):

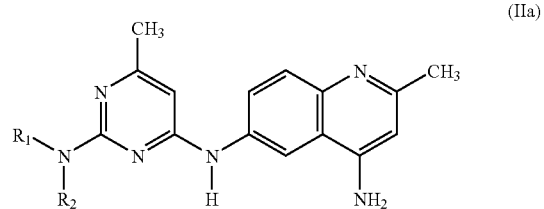

(IIa)

wherein:

$R_1$ to $R_2$ are independently selected from the group consisting of H, —X-Alk, —X-Alk-X', and —X—Y—X'; wherein X is —$CR_7R_8$;

X' is —$CHR_7R_8$;

Alk is a $C_2$-$C_{18}$ substituted or unsubstituted hydrocarbon chain;

Y is a $C_2$-$C_8$ substituted or unsubstituted alkylene chain;

$R_6$ is H or (C1-C4) alkyl; and $R_7$ and $R_8$ are independently selected from the group consisting of H or (C1-C4) alkyl;

or a salt of a compound of formula (IIa).

A preferred embodiment provides a method for treating platelet hyperreactivity, comprising administering to a subject an effective amount of at least one compound having the formula (III):

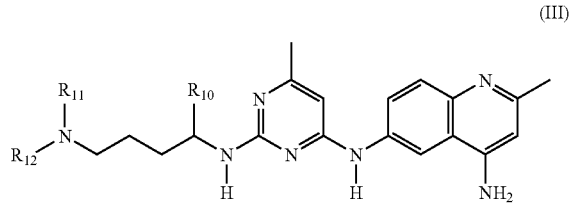

(III)

wherein:

$R_{10}$ to $R_{12}$ are independently selected from the group consisting of H, halo, (C1-C4) alkyl, branched (C3-C4) alkyl, halo (C1-C4) alkyl, (C1-C4) alkoxy, $NO_2$, and $NH_2$;

or a salt of a compound of formula (III).

A preferred embodiment provides a method for treating platelet hyperreactivity, comprising administering to a subject an effective amount of at least one compound having the formula (IV):

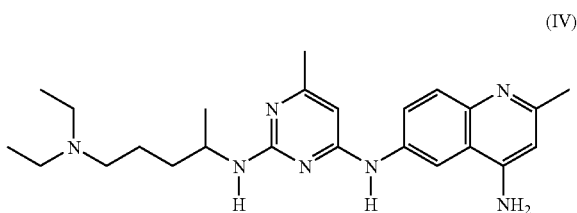

(IV)

or pharmaceutically acceptable salts thereof.

BRIEF DESCRIPTION OF THE DRAWINGS

FIGS. 2A-2D show dose dependent specific inhibition of GEF interaction with Rac1 by Compound NCI23766.

DETAILED DESCRIPTION OF THE PREFERRED EMBODIMENT

Figure 1:
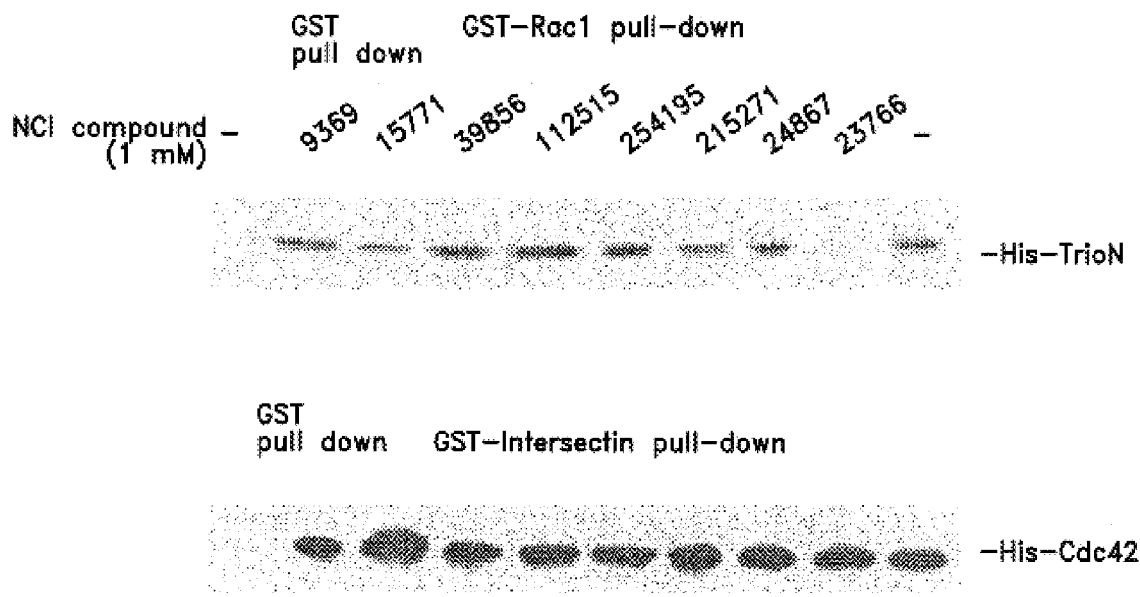
FIG. 1 shows identification of Compound NCI23766 as an inhibitor of Rac1-Trio interaction.

Throughout this document, all temperatures are given in degrees Celsius, and all percentages are weight percentages unless otherwise stated. The following are definitions of terms used in this specification. The initial definition provided for a group or term herein applies to that group or term throughout the present specification, individually or as part of another group, unless otherwise indicated. The following definitions, unless otherwise defined, apply to preferred embodiments.

The terms "active compounds" or "active agents" refer to any one of the agents described by formula I, II, IIa, III, IIIa, or IV.

The term "alkyl" refers to straight or branched chain hydrocarbon groups having 1 to 12 carbon atoms, or more, preferably 1 to 8 carbon atoms. Lower alkyl groups, that is, alkyl groups of 1 to 4 carbon atoms, are most preferred.

The term "substituted alkyl" refers to an alkyl group as defined above having at least one substituent, such as halo, amino, cyano, hydroxy, alkoxy, alkylthio, —NH(alkyl), —NH (cycloalkyl), —N(alkyl)$_2$, —C(=O)H, —CO$_2$H, —CO$_2$-alkyl, cycloalkyl, substituted cycloalkyl, aryl, heteroaryl, or heterocycle. The term "substituted alkyl" also includes an alkyl group as defined above substituted with N(substituted alkyl) or N(substituted alkyl)$_2$, or in other words, the groups (CH$_2$)$_n$NHR' and (CH$_2$)$_n$NR'R", wherein each of R' and R" comprises a substituted alkyl or R' and R" together form a heterocyclo ring.

The term "alkoxy" refers to an alkyl group as defined above bonded through an oxygen (—O—).

The term "alkylthio" refers to an alkyl group as defined above bonded through a sulfur (—S—).

The term "cycloalkyl" refers to fully saturated and partially unsaturated hydrocarbon rings of at least 3, preferably 3 to 9, more preferably 3 to 7, carbon atoms as well as such rings having a fused aryl ring such as indane.

The term "substituted cycloalkyl" refers to such rings having one, two or three substituents, preferably one, such as alkyl, substituted alkyl, alkoxy, alkylthio, halo, hydroxy, cyano, amino, —NH(alkyl), —NH(cycloalkyl), —N(alkyl)$_2$, —CO$_2$H, —CO$_2$-lower alkyl, aryl, heterocyclo, heteroaryl, keto, =N—OH, =N—O-lower alkyl, and a five or six membered ketal, i.e. 1,3-dioxolane or 1,3-dioxane.

The term "halo" refers to fluoro, chloro, bromo and iodo.

The term "aryl" refers to phenyl, 1-naphthyl and 2-naphthyl, with phenyl being preferred. The term "aryl" includes such rings having from zero, one, two or three substituents, such as alkyl, substituted alkyl, alkoxy, alkylthio, halo, hydroxy, nitro, cyano, amino, —NH(alkyl), —NH(cycloalkyl), —N(alkyl)$_2$, —CO$_2$H, —(C=O)alkyl, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The term "heterocyclo" refers to substituted and unsubstituted non-aromatic 3 to 7 membered monocyclic groups, 7 to 11 membered bicyclic groups, and 10 to 15 membered tricyclic groups which have at least one heteroatom (O, S or N) in at least one of the rings. Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing the bicyclic and tricyclic groups may contain only carbon atoms and can be saturated, partially saturated, or unsaturated. The nitrogen and sulfur atoms can optionally be oxidized and the nitrogen atoms can optionally be quaternized. The heterocyclic group can be attached at any available nitrogen or carbon atom. The heterocyclic ring can contain one, two or three substituents, such as halo, amino, cyano, alkyl, substituted alkyl, —NH (alkyl), —NH(cycloalkyl), —N(alkyl)$_2$, alkoxy, alkylthio, hydroxy, nitro, phenyl, benzyl, phenylethyl, phenyloxy, phenylthio, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, heterocyclo, heteroaryl, keto, =N—OH, =N—O-lower alkyl, and a five or six membered ketal, i.e., 1,3-dioxolane or 1,3-dioxane.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups can contain only carbon atoms and can be saturated, partially saturated, or unsaturated. The nitrogen and sulfur atoms can optionally be oxidized and the nitrogen atoms can optionally be quaternized. Heteroaryl groups which are bicyclic or tricyclic must include at least one fully aromatic ring but the other fused ring or rings can be aromatic or non-aromatic. The heteroaryl group can be attached at any available nitrogen or carbon atom of any ring. The heteroaryl ring system can contain one, two or three substituents, such as halo, amino, cyano, alkyl, substituted alkyl, —NH(alkyl), —NH(cycloalkyl), —N(alkyl)$_2$, alkoxy, alkylthio, hydroxy, nitro, phenyl, benzyl, phenylethyl, phenyloxy, phenylthio, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, heterocylco, and heteroaryl.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "substituted imidazole" refers to an imidazole, an aryl-fused imidazole such as benzimidazole, or a heteroaryl-fused imidazole such as a pyridoimidazole which contain one or two substituents, such as hydrogen, alkyl, substituted alkyl, alkoxy, alkylthio, halo, hydroxy, nitro, cyano, amino, —NH(alkyl), —NH(cycloalkyl), —N(alkyl)$_2$, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The term "substituted triazole" refers to a triazole having at least one substituent, such as alkyl, substituted alkyl, alkoxy, alkylthio, halo, hydroxy, nitro, cyano, amino, —NH(alkyl), —NH(cycloalkyl), —N(alkyl)$_2$, —CO$_2$H, —CO$_2$-alkyl, cycloalkyl, substituted cycloalkyl, —(C=O)NH$_2$, —(C=O)NH(alkyl), —(C=O)NH(cycloalkyl), —(C=O)N(alkyl)$_2$, —NH—CH$_2$—CO$_2$H, —NH—CH$_2$—CO$_2$-alkyl, phenyl, benzyl, phenylethyl, phenyloxy, phenylthio, heterocyclo, and heteroaryl.

The terms "(C1-C3) alkyl", "(C1-C4) alkyl", and "(C1-C10) alkyl", when used alone, refer to straight chain alkyl radicals.

The terms "branched (C3-C4) alkyl", and "branched (C3-C6) alkyl" refer to all alkyl isomers containing the designated number of carbon atoms, excluding the straight chain isomers.

The terms "(C1-C4) alkoxy" and "(C1-C7) alkoxy" refer to straight or branched chain alkoxy groups.

The term "halo (C1-C7) alkyl" refers to a (C1-C7) alkyl group, straight chain or branched, substituted with one or more halo groups.

The term "substituted phenyl" used alone or in combination with other terms, as in "substituted phenylthio" or "substituted phenylsulfonyl", refers to phenyl substituted with up to three groups, such as halo, (C1-C10) alkyl, branched (C3-C6) alkyl, halo (C1-C7) alkyl, hydroxy (C1-C7) alkyl, (C1-C7) alkoxy, halo (C1-C7) alkoxy, phenoxy, phenyl, NO$_2$, OH, CN, (C1-C4) alkanoyloxy, or benzyloxy.

The term "substituted phenoxy" refers to phenoxy substituted with at least one group, such as halo, (C1-C10) alkyl, branched (C3-C6) alkyl, halo (C1-C7) alkyl, hydroxy (C1-C7) alkyl, (C1-C7) alkoxy, halo (C1-C7) alkoxy, phenoxy, phenyl, NO$_2$, OH, CN, (C1-C4) alkanoyloxy, or benzyloxy.

The terms "substituted naphthyl", "substituted pyridyl" and "substituted furanyl" refer to these ring systems substituted with at least one group such as, halo, halo (C1-C4) alkyl, CN, NO$_2$, (C1-C4) alkyl, (C3-C4) branched alkyl, phenyl, (C1-C4) alkoxy, or halo (C1-C4) alkoxy.

The term "unsaturated hydrocarbon chain" refers to a hydrocarbon chain containing one or two sites of unsaturation.

The preferred embodiments provide quinoline derivatives of the following formula (I) or salts thereof, for use as inhibitors of RhoGTPases, especially Rac1GTPase:

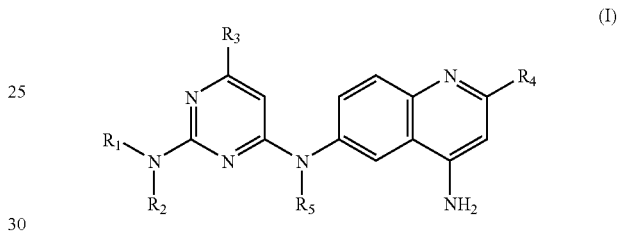

(I)

wherein: $R_1$ to $R_5$ are independently: H, halo, (C1-C4) alkyl, branched (C3-C4) alkyl, halo (C1-C4) alkyl, (C1-C4) alkoxy, NO$_2$, NH$_2$, —X-Alk, —X-Alk-X, —X—Y—X, —NR$_6$ or O—R$_6$, wherein X is O, NR$_6$, or CR$_7$R$_8$;

Alk is a C2-C18 saturated or unsaturated hydrocarbon chain, straight chain or branched, optionally substituted with halo, halo (C1-C4) alkoxy, (C3-C8) cycloalkyl, hydroxy, or acetyl;

Y is an alkylene chain 2 to 8 carbon atoms long, that optionally includes an O, S, SO, SO$_2$, or NR$_6$ group, and optionally includes a saturated or unsaturated carbocyclic ring comprising three to seven carbon atoms, and optionally is substituted with (C1-C3) alkyl, (C2-C4) phenyl, (C3-C8) cycloalkyl, hydroxy, halo, or (C1-C4) acyl; and Ar is 1,3-benzodioxolyl, fluorenyl, pyridyl, substituted pyridyl, indolyl, furanyl, substituted furanyl, thienyl, optionally substituted with CH$_2$ or Cl, thiazolyl, cyclopentyl, 1-methylcyclopentyl, cyclohexenyl (tetrahydrophenyl), cyclohexyl (hexahydrophenyl), naphthyl, substituted naphthyl, dihydronaphthyl, tetrahydronaphthyl, or decahydronaphthyl;

$R_6$ is H, (C1-C4) alkyl, or acetyl;

$R_7$ and $R_8$ are independently H, (C1-C4) alkyl, (C1-C4) acyl, halo, —OH, O—Y—Ar, or —NR$_9$—Y—Ar; and $R_6$ is H, (C1-C4) alkyl, or acetyl.

or a salt of a compound of formula (I).

Preferably at least two of $R_1$ to $R_5$ being H or CH$_3$, and at least one of $R_1$ to $R_2$ is —X-Alk, —X-Alk-X or —X—Y—X, —NR$_6$ or O—R$_6$ and the rest of $R_1$ to $R_5$ are H or CH$_3$; wherein:

X is O, NR$_6$, or CR$_7$R$_8$;

Alk is a C2-C18 saturated or unsaturated hydrocarbon chain, straight chain or branched, optionally substituted with halo, halo (C1-C4) alkoxy, (C3-C8) cycloalkyl, hydroxy, or acetyl;

Y is an alkylene chain 2 to 8 carbon atoms long, that optionally includes an O, S, SO, SO$_2$, or NR$_6$ group, and optionally includes a saturated or unsaturated carbocyclic ring comprising three to seven carbon atoms, and optionally is substituted with (C1-C3) alkyl, (C2-C4) phenyl, (C3-C8) cycloalkyl, hydroxy, halo, or (C1-C4) acyl; and Ar is 1,3-benzodioxolyl, fluorenyl, pyridyl, substituted pyridyl, indolyl, furanyl, substituted furanyl, thienyl, optionally substituted with CH$_2$ or Cl, thiazolyl, cyclopentyl, 1-methylcyclopentyl, cyclohexenyl (tetrahydrophenyl), cyclohexyl (hexahydrophenyl), naphthyl, substituted naphthyl, dihydronaphthyl, tetrahydronaphthyl, or decahydronaphthyl;

R$_6$ is H, (C1-C4) alkyl, or acetyl;

R$_7$ and R$_8$ are independently H, (C1-C4) alkyl, (C1-C4) acyl, halo, —OH, O—Y—Ar, or —NR$_9$—Y—Ar; and R$_9$ is H, (C1-C4) alkyl, or acetyl.

Preferably, the preferred embodiments provide compounds of the formula (II) or salts thereof, for use as inhibitors of RhoGTPases:

(II)

wherein:

R$_1$ to R$_2$ are independently: H, halo, (C1-C4) alkyl, branched (C3-C4) alkyl, halo (C1-C4) alkyl, (C1-C4) alkoxy, NO$_2$, NH$_2$, —X-Alk, —X-Alk-X, —X—Y—X, —NR$_6$, or O—R$_6$, wherein X is O, NR$_6$, or CR$_7$R$_8$;

Alk is a C2-C18 saturated or unsaturated hydrocarbon chain, straight chain or branched, optionally substituted with halo, halo (C1-C4) alkoxy, (C3-C8) cycloalkyl, hydroxy, or acetyl;

Y is an alkylene chain 2 to 8 carbon atoms long, that optionally includes an O, S, SO, SO$_2$, or NR$_6$ group, and optionally includes a saturated or unsaturated carbocyclic ring comprising three to seven carbon atoms, and optionally is substituted with (C1-C3) alkyl, (C2-C4) phenyl, (C3-C8) cycloalkyl, hydroxy, halo, or (C1-C4) acyl; and Ar is 1,3-benzodioxolyl fluorenyl, pyridyl, substituted pyridyl, indolyl, furanyl, substituted furanyl, thienyl, optionally substituted with CH$_2$ or Cl, thiazolyl, cyclopentyl, 1-methylcyclopentyl, cyclohexenyl (tetrahydrophenyl), cyclohexyl (hexahydrophenyl), naphthyl, substituted naphthyl, dihydronaphthyl, tetrahydronaphthyl, or decahydronaphthyl;

R$_6$ is H, (C1-C4) alkyl, or acetyl;

R$_7$ and R$_8$ are independently H, (C1-C4) alkyl, (C1-C4) acyl, halo, —OH, O—Y—Ar, or —NR$_9$—Y—Ar; and R$_9$ is H, (C1-C4) alkyl, or acetyl.

or a salt of a compound of formula (II).

Preferably, the preferred embodiments provide compounds of the formula (IIa) or salts thereof, for use as inhibitors of RhoGTPases:

(IIa)

wherein:

R$_1$ to R$_2$ are independently: H, —X-Alk, —X-Alk-X', or —X—Y—X' wherein

X is —CR$_7$R$_8$;

X' is —CHR$_7$R$_8$;

Alk is a C2-C18 saturated or unsaturated hydrocarbon chain, straight chain or branched, optionally substituted with halo, halo (C1-C4) alkoxy, (C3-C8) cycloalkyl, hydroxy, or acetyl;

Y is an alkylene chain 2 to 8 carbon atoms long, that optionally includes an NR$_6$ group;

R$_6$ is H or (C1-C4) alkyl; and

R$_7$ and R$_8$ are independently H or (C1-C4) alkyl;

or a salt of a compound of formula (IIa).

The preferred embodiments provide compounds of the formula (III) or salts thereof, for use as inhibitors of Rho GTPases:

(III)

wherein:

R$_{10}$ to R$_{12}$ are independently: H, halo, (C1-C4) alkyl, branched (C3-C4) alkyl, halo (C1-C4) alkyl, (C1-C4) alkoxy, NO$_2$, or NH$_2$;

or a salt of a compound of formula (III).

The preferred embodiments provide compounds of the formula (IIIa) or salts thereof, for use as inhibitors of Rho GTPases:

(IIIa)

wherein:

R$_{10}$ to R$_{12}$ are independently: H, (C1-C4) alkyl, or branched (C3-C4) alkyl;

or a salt of a compound of formula (IIIa).

The preferred embodiments provide compounds of the formula (IV) or salts thereof, for use as inhibitors of Rho GTPases:

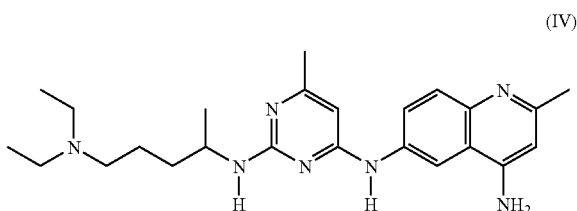

(IV)

or a salt of a compound of formula (IV).

The pharmaceutical compositions of the preferred embodiments comprise a disease inhibiting and pharmaceutically acceptable amount of a compound of formula I, II, IIa, III, IIIa, or IV, or N6-(2-((4-(diethylamino)-1-methylbutyl)amino)-6-methyl-4-pyrimidinyl)-2-methyl-4,6-quinolinediamine, in combination with a pharmaceutically-acceptable carrier.

A pharmaceutical composition of the preferred embodiments can comprise at least about 1% by weight of a compound of formula I, II, IIa, III, IIIa, or IV, or N-6-(2-((4-(diethylamino)-1-methylbutyl)amino)-6-methyl-4-pyrimidinyl)-2-methyl-4,6-quinolinediamine (e.g., formula IV).

A pharmaceutical compositions of the preferred embodiments can comprise a compound of formula I, II, IIa, III, IIIa, or IV, or $N^6$-(2-((4-(diethylamino)-1-methylbutyl)amino)-6-methyl-4-pyrimidinyl)-2-methyl-4,6-quinolinediamine (e.g., formula IV) further comprising a pharmaceutically active compound.

The pharmaceutical combinations of the preferred embodiments comprise at least about 1% by weight of a compound of formula I, II, IIa, III, IIIa, or IV, or $N^6$-(2-((4-(diethylamino)-1-methylbutyl)amino)-6-methyl-4-pyrimidinyl)-2-methyl-4,6-quinolinediamine (e.g., formula IV), further comprising a pharmaceutically active compound.

The pharmaceutical compositions of the preferred embodiments comprise a amount of a Rho family GTPase-regulating active compound for controlling platelet hyperreactivity in combination with a pharmaceutically-acceptable carrier.

In another embodiment, the pharmaceutical combinations of the preferred embodiments comprise at least about 1% by weight of a Rho family GTPase-regulating active compound further comprising additional pharmaceutical agent for platelet hyperreactivity and, preferably, in combination with a pharmaceutically-acceptable carrier.

The pharmaceutical methods of the preferred embodiments comprise administering N6-(2-((4-(diethylamino)-1-methylbutyl)amino)-6-methyl-4-pyrimidinyl)-2-methyl-4,6-quinolinediamine to a subject in need of such treatment with a therapeutic amount of a compound of formula I, II, IIa, III, IIIa, or IV, or of a combination described above.

As used herein, the terms "Ras or Ras superfamily proteins" encompass a large family of GTP binding/GTP hydrolyzing monomeric proteins. Ras family includes the Ras, Rho, Rab, Arf, and Ran subfamilies of GTPases.

The terms "Rho GTPases" or "Rho family GTPases" refer to a subfamily of Ras superfamily and are small, membrane-bound, Ras-related GTP-binding proteins that function by binding and hydrolyzing GTP. Rho GTPases function as molecular switches, cycling between an inactive GDP-bound conformation and an active GTP-bound conformation and include RhoA, RhoB, RhoC, Cdc42, Rac1, Rac2, Rac3, TC10, RhoG, RhoD, Chp, WRCH1, TCL, and RIF.

A protein or polypeptide sequence of a Ras-related protein includes variants or fragments thereof derived from any species, particularly mammalian, including bovine, ovine, porcine, murine, equine, and preferably human, from any source whether natural, synthetic, semi-synthetic, or recombinant.

The terms "Rac GTPase" or "Rac protein or polypeptide" refer to Rac1, Rac2, and/or Rac3.

Methods and compositions are described that affect the GTPase activity of members of the Ras superfamily, preferably Rac; such compositions include compounds that modulate the GTPase activity. Preferably, the indication associated with GTPase activity is selected from the group consisting of platelet hyperreactivity, hypertension, atherosclerosis, restenosis, cerebral ischemia, cerebral vasospasm, neuronal degeneration, spinal cord injury, cancer of the breast, colon, prostate, ovaries, brain or lung, thrombotic disorders, asthma, glaucoma, osteoporosis and erectile dysfunction. More preferably, the indication associated with GTPase activity is platelet hyperreactivity.

One embodiment provides for a method for controlling platelet hyperreactivity by administering in a subject having such condition an effective amount of an active compound as defined herein.

Another embodiment provides for the use of an effective amount an active compound as defined herein for the preparation of pharmaceutical composition for the treatment of a disease associated with platelet hyperreactivity.

As used herein, "treatment" or "treating" includes both therapeutic and prophylactic treatments. Accordingly, the compounds can be used at very early stages of a disease, or before early onset, or after significant progression. The term "treatment" or "treating" designates in particular a reduction of the burden in a patient.

Modulation of Pathways

Methods and compositions are described that affect the GTPase activity of members of the Ras superfamily, preferably Rac; such compositions include compounds that modulate the GTPase activity, including platelet hyperreactivity.

Chimeric peptides capable of regulating GTPases and methods of targeting individual GTPases by using GTPase-activating proteins are described in U.S. patent application Ser. No. 10/918,648, filed Aug. 12, 2004, herein incorporated by reference.

Methods and pharmaceutical compositions for enhancing stem cell engraftment, comprising the administration of an effective amount of a modulator of RhoGTPases are described in U.S. patent application Ser. No. 11/003,935, filed Dec. 3, 2004, herein incorporated by reference.

Methods and compositions that affect the GTP-binding activity of members of the Ras superfamily GTPases, along with uses for the compounds including screening for compounds that recognize Rac GTPase, and methods of treating pathological conditions associated or related to a Ras superfamily GTPase are described in U.S. patent application Ser. No. 10/994,165, filed Nov. 19, 2004, herein incorporated by reference.

A crystal structure of Rac-1 GTPase is described in U.S. Patent Application No. 60/703,587, filed Jul. 29, 2004, herein incorporated by reference.

Another aspect of the preferred embodiments relates to the regulation of biological pathways in which a GTPase is involved, particularly pathological conditions, e.g., platelet hyperreactivity, cell proliferation (e.g., cancer), growth control, morphogenesis, stress fiber formation, and integrin-mediated interactions, such as embryonic development, tumor cell growth and metastasis, programmed cell death, hemostasis, leukocyte homing and activation, bone resorption, clot retraction, and the response of cells to mechanical stress. Thus, the preferred embodiments relate to all aspects of a method of modulating an activity of a Rac polypeptide comprising, administering an effective amount of an active agent, an effective amount of a compound which modulates the activity of a Rac polypeptide, or combination thereof. The activity of Rac which is modulated can include: GTP binding, GDP binding, GTPase activity, integrin binding, coupling or binding of Rac to receptor or effector-like molecules (such as integrins, growth factor receptors, tyrosine kinases, PI-3K, PIP-5K, etc.). Increasing, reducing, antagonizing, or promoting Rac can modulate the activity. The modulation of Rac can be measured by assay for GTP hydrolysis, binding to Rac-GEF, etc. An effective amount is any amount which, when administered, modulates the Rac activity. The activity can be modulated in a cell, a tissue, a whole organism, in situ, in vitro (test tube, a solid support, etc.), in vivo, or in any desired environment.

The modulation of activity by an active agent, or derivatives thereof, can be measured according to various known procedures. A compound can be added at any time during the method to determine its effect on the platelet hyperreactivity activity of an active agent. Various cell lines can also be used.

Other assays for Rac-mediated signal transduction can be accomplished according to procedures known in the art, e.g., as described in U.S. Pat. Nos. 5,141,851; 5,420,334; 5,436,128; and 5,482,954, all of which are incorporated herein by reference in their entirety. In addition, peptides that inhibit the interaction, e.g., binding, between an active agent and a G-protein, such as Rac, can be identified.

The preferred embodiments also relate to a method of testing for and identifying an agent which modulates the activity of RacGTPase, or a biologically-active fragment thereof, or which modulates the binding between an active agent, or a biologically-active fragment thereof, and a GTPase, or a biologically-active fragment thereof, to which it binds. The method comprises contacting the active agent and Rac GTPase with an agent to be tested and then detecting the presence or amount of binding between the active agent and GTPase, or an activity of the active agent.

By modulating, it is meant that addition of the agent affects the activity or binding. The binding or activity modulation can be affected in various ways, including inhibiting, blocking, preventing, increasing, enhancing, or promoting it. The binding or activity effect does not have to be achieved in a specific way, e.g., it can be competitive, noncompetitive, allosteric, sterically hindered, via cross-linking between the agent and the GEF or GTPase, etc. The agent can act on either the active agent or GTPase. The agent can be an agonist, an antagonist, or a partial agonist or antagonist. The presence or amount of binding can be determined in various ways, e.g., directly or indirectly by assaying for an activity promoted or inhibited by the active agent, such as guanine nucleotide exchange, GTP hydrolysis, oncogenic transformation, etc. Such assays are described above and below, and are also known in the art. The agent can be obtained and/or prepared from a variety of sources, including natural and synthetic. It can comprise, e.g., amino acids, lipids, carbohydrates, organic molecules, nucleic acids, inorganic molecules, or mixtures thereof.

The agent can be added simultaneously or sequentially. For example, the agent can be added to the active agent and then the resultant mixture can be further combined with the GTPase. The method can be carried out in liquid on isolated components, on a matrix (e.g., filter paper, nitrocellulose, agarose), in cells, on tissue sections, etc.

The method further relates to obtaining or producing agents that have been identified according to the above-described method. The preferred embodiments also relate to products identified in accordance with such methods.

The preferred embodiments thus also relate to the treatment and prevention of diseases and pathological conditions associated with Rac-mediated signal transduction, e.g., platelet hyperreactivity, cancer, diseases associated with abnormal cell proliferation, and the like. For example, the preferred embodiments relate to a method of treating platelet hyperreactivity comprising administering, to a subject in need of treatment, an amount of a compound effective to treat the disease, where the compound is an active agent. Treating the disease can mean, delaying its onset, delaying the progression of the disease, improving or delaying clinical and pathological signs of disease.

A regulator compound, or mixture of compounds, can be synthetic, naturally-occurring, or a combination. A regulator compound can comprise amino acids, nucleotides, hydrocarbons, lipids, polysaccharides, etc. A regulator compound is preferably a regulator of Rac GTPase. To treat the disease, the compound, or mixture, can be formulated into pharmaceutical composition comprising a pharmaceutically acceptable carrier and other excipients as apparent to the skilled worker. Such composition can additionally contain effective amounts of other compounds, especially for treatment of platelet hyperreactivity.

Conditions

The compounds of preferred embodiments can be used in relation to disorders involving platelet hyperreactivity. Platelet hyperreactivity can result in deposition of platelets on the surface of damaged blood vessels. When too much deposition occurs or when deposition occurs in a smaller vessel, this can result in occlusion of the vessel. In patients with cardiovascular disease and stroke, this can lead to arterial thrombosis. Platelet hyperactivity can include increased platelet adhesion, aggregation, thromboxane production, increased plasma levels of platelet-specific proteins, and increased platelet turnover. Disorders involving platelet hyperreactivity include, but are not limited to, cardiovascular disease, stroke, arterial thrombosis, Kawasaki syndrome, and moyomoya.

The Rac GTPases, including Rac1 and Rac 2, are members of the Ras related family of Rho proteins, and have been shown to be involved in the regulation of cell spreading, adhesion and actin cytoskeleton reorganization as well as secretion in hematopoietic cells. Adhesion of platelets to vascular matrix containing collagen or fibrinogen and subsequent granular secretion are the critical steps that lead to platelet aggregation.

Previous methods of treatment for these disorders have a number of drawbacks, including the side effects of aspirin, the lack of testing of thienopyridine derivatives in children, and glycoprotein IIb/IIIa inhibitors are complicated to use and have had limited usefulness except in short term clinical trials. Because of this, this approach can bring about a highly novel method of antiplatelet therapy that can have a broad application in prevention and management of thrombosis in pediatric and adult patients.

The compounds can be administered to treat a specific area of a vein or artery by any method known to one of skill in the art. For example, the compounds can be injected into an artery, vein, or organ near the site of deposition. Alternatively, the compounds can be used in combination with another treatment method for any of the disorders of involving platelet hyperreactivity. Alternatively, a pump can be administered to pump the compounds into the affected area using any method known to one of skill in the art.

In one embodiment, the compounds are administered to prevent the depositions of platelets in a patient with a family history of cardiovascular disease, a patient with a family history of stroke, or a family history of any of the diseases associated with platelet hyperreactivity and/or deposition, known to one of skill in the art. The compounds can also be used before or after a surgery which might increase the risk of platelet hyperreactivity.

The compounds of preferred embodiments can be used in relation to disorders arising from bone marrow cells. In normal bone marrow, the myelocytic series (polymorphonuclear cells) make up approximately 60% of the cellular elements, and the erythrocytic series, 20-30%. Lymphocytes, monocytes, reticular cells, plasma cells and megakaryocytes together constitute 10-20%. Lymphocytes make up 5-15% of normal adult marrow. In the bone marrow, cell types are add mixed so that precursors of red blood cells (erythroblasts), macrophages (monoblasts), platelets (megakaryocytes), polymorphoneuclear leukocytes (myeloblasts), and lymphocytes (lymphoblasts) can be visible in one microscopic field. In addition, stem cells exist for the different cell lineages, as well as a precursor stem cell for the committed progenitor cells of the different lineages. The various types of cells and stages of each are known to the person of ordinary skill in the art and are found, for example, in *Immunology, Imunopathology and Immunity*, Fifth Edition, Sell et al. Simon and Schuster (1996), which is incorporated herein by reference in its entirety. Accordingly, the preferred embodiments are directed to disorders arising from these cells. These disorders include but are not limited to the following: diseases involving hematopoietic stem cells; committed lymphoid progenitor cells; lymphoid cells including B and T-cells; committed myeloid progenitors, including monocytes, granulocytes, and megakaryocytes; and committed erythroid progenitors. These include but are not limited to the leukemias, including B-lymphoid leukemias, T-lymphoid leukemias, undifferentiated leukemias; erythroleukemia, megakaryoblastic leukemia, monocytic; [leukemias are encompassed with and without differentiation]; chronic and acute lymphoblastic leukemia, chronic and acute lymphocytic leukemia, chronic and acute myelogenous leukemia, lymphoma, myelo dysplastic syndrome, chronic and acute myeloid leukemia, myelomonocytic leukemia; chronic and acute myeloblastic leukemia, chronic and acute myelogenous leukemia, chronic and acute promyelocytic leukemia, chronic and acute myelocytic leukemia, hematologic malignancies of monocyte-macrophage lineage, such as juvenile chronic myelogenous leukemia; secondary AML, antecedent hematological disorder; refractory anemia; aplastic anemia; reactive cutaneous angioendotheliomatosis; fibrosing disorders involving altered expression in dendritic cells, disorders including systemic sclerosis, E-M syndrome, epidemic toxic oil syndrome, eosinophilic fasciitis localized forms of scleroderma, keloid, and fibrosing colonopathy; angiomatoid malignant fibrous histiocytoma; carcinoma, including primary head and neck squamous cell carcinoma; sarcoma, including kaposi's sarcoma; fibroadenoma and phyllodes tumors, including mammary fibroadenoma; stromal tumors; phyllodes tumors, including histiocytoma; erythroblastosis; neurofibromatosis; diseases of the vascular endothelium; demyelinating, particularly in old lesions; gliosis, vasogenic edema, vascular disease, Alzheimer's and Parkinson's disease; T-cell lymphomas; B-cell lymphomas.

The compounds of preferred embodiments can be used in relation to disorders involving the spleen. Disorders involving the spleen include, but are not limited to, splenomegaly, including nonspecific acute splenitis, congestive spenomegaly, and spenic infarcts; neoplasms, congenital anomalies, and rupture. Disorders associated with splenomegaly include infections, such as nonspecific splenitis, infectious mononucleosis, tuberculosis, typhoid fever, brucellosis, cytomegalovirus, syphilis, malaria, histoplasmosis, toxoplasmosis, kala-azar, trypanosomiasis, schistosomiasis, leishmaniasis, and echinococcosis; congestive states related to partial hypertension, such as cirrhosis of the liver, portal or splenic vein thrombosis, and cardiac failure; lymphohematogenous disorders, such as Hodgkin disease, non-Hodgkin lymphomas/leukemia, multiple myeloma, myeloproliferative disorders, hemolytic anemias, and thrombocytopenic purpura; immunologic-inflammatory conditions, such as rheumatoid arthritis and systemic lupus erythematosus; storage diseases such as Gaucher disease, Niemann-Pick disease, and mucopolysaccharidoses; and other conditions, such as amyloidosis, primary neoplasms and cysts, and secondary neoplasms.

The compounds of preferred embodiments can be used in relation to disorders involving blood vessels. Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopcricytoma; and pathology of therapeutic interventions in vascular disease, such as balloon angioplasty and related techniques and vascular replacement, such as coronary artery bypass graft surgery.

The compounds of preferred embodiments can be used in relation to disorders involving red cells. Disorders involving red cells include, but are not limited to, anemias, such as hemolytic anemias, including hereditary spherocytosis, hemolytic disease due to erythrocyte enzyme defects: glucose-6-phosphate dehydrogenase deficiency, sickle cell disease, thalassemia syndromes, paroxysmal nocturnal hemoglobinuria, immunohemolytic anemia, and hemolytic anemia resulting from trauma to red cells; and anemias of diminished erythropoiesis, including megaloblastic anemias, such as anemias of vitamin B12 deficiency: pernicious anemia, and anemia of folate deficiency, iron deficiency anemia, anemia of chronic disease, aplastic anemia, pure red cell aplasia, and other forms of marrow failure.

The compounds of preferred embodiments can be used in relation to disorders involving B-cells. Disorders involving B-cells include, but are not limited to precursor B-cell neoplasms, such as lymphoblastic leukemia/lymphoma. Peripheral B-cell neoplasms include, but are not limited to, chronic lymphocytic leukemia/small lymphocytic lymphoma, follicular lymphoma, diffuse large B-cell lymphoma, Burkitt lymphoma, plasma cell neoplasms, multiple myeloma, and related entities, lymphoplasmacytic lymphoma (Waldenstrom macroglobulinemia), mantle cell lymphoma, marginal zone lymphoma (MALToma), and hairy cell leukemia.

The compounds of preferred embodiments can be used in relation to disorders related to reduced platelet number. Disorders related to reduced platelet number, thrombocytopenia, include idiopathic thrombocytopenic purpura, including acute idiopathic thrombocytopenic purpura, drug-induced thrombocytopenia, HIV-associated thrombocytopenia, and thrombotic microangiopathies: thrombotic thrombocytopenic purpura and hemolytic-uremic syndrome.

The compounds of preferred embodiments can be used in relation to disorders involving precursor T-cell neoplasms. Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Szary syndrome, peripheral T-cell lymphoma, unspecified, angioimmunoblastic T-cell lymphoma, angiocentric lymphoma (NK/T-cell lymphoma4a), intestinal T-cell lymphoma, adult T-cell leukemia/lymphoma, and anaplastic large cell lymphoma.

The preferred embodiments relate to methods of treatment of disorders involving T-cells include, but are not limited to, cell-mediated hypersensitivity, such as delayed type hypersensitivity and T-cell-mediated cytotoxicity, and transplant rejection; autoimmune diseases, such as systemic lupus erythematosus, Sjogren syndrome, systemic sclerosis, inflammatory-myopathies, mixed connective tissue disease, and polyarteritis nodosa and other vasculitides; immunologic deficiency syndromes, including but not limited to, primary immunodeficiencies, such as thymic hypoplasia, severe combined immunodeficiency diseases, and AIDS; leukopenia; reactive (inflammatory) proliferations of white cells, including but not limited to, leukocytosis, acute nonspecific lymphadenitis, and chronic nonspecific lymphadenitis; neoplastic proliferations of white cells, including but not limited to lymphoid neoplasms, such as precursor T-cell neoplasms, such as acute lymphoblastic leukemia/lymphoma, peripheral T-cell and natural killer cell neoplasms that include peripheral T-cell lymphoma, unspecified, adult T-cell leukemia/lymphoma, mycosis fungoides and Szary syndrome, and Hodgkin disease.

Pharmaceutical Compositions

The active compounds can be incorporated into pharmaceutical compositions suitable for administration to a subject, e.g., a human. Such compositions typically comprise the compound and a pharmaceutically acceptable carrier.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the preferred embodiments. Supplementary active compounds can also be incorporated into the compositions. A pharmaceutical composition of the preferred embodiments is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid, buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes) can also be used as pharmaceutically acceptable carriers. These can be prepared according to methods known to those skilled in the art.

It is especially advantageous to formulate oral or parenteral compositions in dosage unit form for ease of administration and uniformity of dosage. "Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the preferred embodiments, a therapeutically effective amount of one, two, or more of the active agents of the preferred embodiments is administered to a subject afflicted with a disease or disorder related to Rho family GTPases, or to a tissue which has such disease or disorder. The active agents of the preferred embodiments can be administered in accordance with the method of the preferred embodiments either alone of in combination with other known therapies. When co-administered with one or more other therapies, the active agents of the preferred embodiments can be administered either simultaneously with the other treatment(s), or sequentially. If administered sequentially, the attending physician will decide on the appropriate sequence of administering the active agents of the preferred embodiments in combination with the other therapy.

Generally, a therapeutically effective amount of active agent (i.e., an effective dosage) ranges from about 0.001 to about 5000 mg/kg body weight, more preferably about 0.01 to about 1000 mg/kg body weight, more preferably about 0.01 to about 500 mg/kg body weight, more preferably about 0.01 to about 250 mg/kg body weight, more preferably about 0.01 to about 100 mg/kg body weight, more preferably about 0.001 to about 60 mg/kg body weight, more preferably about 0.01 to about 25 mg/kg body weight, more preferably about 0.1 to about 20 mg/kg body weight, and even more preferably about 1 to about 10 mg/kg, about 2 to about 9 mg/kg, about 3 to about 8 mg/kg, about 4 to about 7 mg/kg, or about 5 to about 6 mg/kg body weight.

The skilled artisan will appreciate that certain factors can influence the dosage required to effectively treat a subject, including but not limited to the severity of the disease or disorder, previous treatments, the general health and/or age of the subject, and other diseases present. Moreover, treatment of a subject with a therapeutically effective amount can include a single treatment or, preferably, can include a series of treatments. In a preferred example, a subject is treated in the range of between about 0.1 to about 20 mg/kg body weight, one time per week for between about 1 to about 10 weeks, preferably between about 2 to about 8 weeks, more preferably between about 3 to about 7 weeks, and even more preferably for about 4, 5, or 6 weeks. It will also be appreciated that the effective dosage used for treatment can increase or decrease over the course of a particular treatment. Changes in dosage can result and become apparent from the results of diagnostic assays as described herein.

The preferred embodiments encompass one or more additional agents that modulate expression or activity of Rac GTPase. An agent can, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Based on these data, one embodiment is an improved method for treatment of tumors comprising administration of a pharmaceutically effective quantity of active agent or its pharmaceutically acceptable salts or esters, active agent analogs or their pharmaceutically acceptable salts or esters, or a combination thereof.

The compositions and preparations described preferably contain at least about 0.1% of active agent. The percentage of the compositions and preparations can, of course, be varied, and can contain between about 2% and 60% of the weight of the amount administered. Preferably, the percentage of the compositions and preparations can contain between about 2, 5, 10, or 15% and about 30, 35, 40, 45, 50, 55, or 60% of the weight of the amount administered. The amount of active compounds in such pharmaceutically useful compositions and preparations is such that a suitable dosage will be obtained.

The active agent form salts, which are also within the scope of the preferred embodiments. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (i.e., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

The active agent which contain a basic moiety, such as, but not limited to an amine or a pyridine or imidazole ring, can form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The active agents which contain an acidic moiety, such as, but not limited to a carboxylic acid, can form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups can be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Prodrugs and solvates of the compounds of the preferred embodiments are also contemplated herein. The term "prodrug", as employed herein, denotes a compound which, upon administration to a subject, undergoes chemical conversion by metabolic or chemical processes to yield a compound of the active agent, and/or a salt and/or solvate thereof. Solvates of the active agent are preferably hydrates.

Active agent, and salts thereof, can exist in their tautomeric form (for example, as an amide or imino ether). All such tautomeric forms are contemplated herein as part of the preferred embodiments.

All stereoisomers of the present compounds, such as those, for example, which can exist due to asymmetric carbons on any of the substituents, including enantiomeric forms (which can exist even in the absence of asymmetric carbons) and diastereomeric forms, are contemplated and within the scope of the preferred embodiments. Individual stereoisomers of the compounds of the preferred embodiments can, for example, be substantially free of other isomers, or can be admixed, for example, as racemates or with all other or other selected, stereoisomers. The chiral centers of the preferred embodiments can have the S or R configuration as defined by the IUPAC 1974 Recommendations.

When the compounds according to the preferred embodiments are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The pharmaceutically acceptable salts are prepared by reacting the active agent with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol, etc. Mixture of solvents can be used. Organic bases like lysine, arginine, diethanolamine, choline, guandine and their derivatives etc. can also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents can also be used.

As indicated above, a further object of the preferred embodiments relates to a pharmaceutical composition comprising at least one compound of formula I, II, IIa, III, IIIa, or IV, as defined above, and a pharmaceutically acceptable vehicle or support.

The compounds can be formulated in various forms, including solid and liquid forms, such as tablets, gel, syrup, powder, aerosol, etc.

The compositions of the preferred embodiments can contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds of formula I, II, IIa, III, IIIa, or IV are administered will vary according to the dosage form, mode of administration, the condition being treated and particulars of the patient being treated. Accordingly, optimal therapeutic concentrations will be best determined at the time and place through routine experimentation.

The compounds according to the preferred embodiments can also be used enterally. Orally, the compounds according to the preferred embodiments are suitable administered at the rate of about 100 µg to about 100 mg per day per kg of body weight. Preferably, orally, the compounds according to the preferred embodiments are suitable administered at the rate of about 100, 150, 200, 250, 300, 350, 400, 450, or 500 µg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; a preferred method of administration consists in using a suitable form containing from about 1 mg to about 500 mg of active substance. Preferably, a method of administration consists in using a suitable form containing from about 1, 2, 5, 10, 25, or 50 mg to about 100, 200, 300, 400, 500 mg of active substance.

The compounds according to the preferred embodiments can also be administered parenterally in the form of solutions or suspensions for intravenous or intramuscular perfusions or injections. In that case, the compounds according to the preferred embodiments are generally administered at the rate of about 10 µg to about 10 mg per day per kg of body weight; a preferred method of administration consists of using solutions or suspensions containing approximately from about 0.01 mg to about 1 mg of active substance per ml. Preferably, the compounds according to the preferred embodiments are generally administered at the rate of about 10, 20, 30, 40, 50, 60, 70, 80, 90, or 100 μg to 1, 2, 3, 4, 5, 6, 7, 8, 9, or 10 mg per day per kg of body weight; a preferred method of administration consists of using solutions or suspensions containing approximately from about 0.01, 0.02, 0.03, 0.04, or 0.5 mg to about 0.1, 0.2, 0.3, 0.4, 0.5, 0.6, 0.7, 0.8, 0.9, or 1 mg of active substance per ml.

Pharmaceutical Administration

The active compounds of the preferred embodiments can be administered according to various routes, typically by injection, such as local or systemic injection(s). Intratumoral injections are preferred for treating existing cancers. However, other administration routes can be used as well, such as intramuscular, intravenous, intradermic, subcutaneous, etc. Furthermore, repeated injections can be performed, if needed, although it is believed that limited injections will be needed in view of the efficacy of the compounds.

It is contemplated that such target cells can be located within an animal or human patient, in which case a safe and effective amount of the complex, in pharmacologically acceptable form, would be administered to the patient. Generally speaking, it is contemplated that useful pharmaceutical compositions of the preferred embodiments will include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the patient or animal under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The examples are illustrative of the types of compounds to be used in the method claimed herein; the list is not exhaustive. Derivatives of the above compounds that fit the criteria of the claims are preferably also be considered when choosing an active compound.

The compound are preferably administered such that a therapeutically effective concentration of the compound is in contact with the affected cells of the body. The dose administered to an animal, particularly a human, in the context of the preferred embodiments is preferably sufficient to effect a therapeutic response in the animal over a reasonable period of time. The dose will be determined by the strength of the particular compound employed and the condition of the animal, as well as the body weight of the animal to be treated. The existence, nature, and extent of any adverse side effects that might accompany the administration of a particular compound also will determine the size of the dose and the particular route of administration employed with a particular patient. In general, the compounds of the preferred embodiments are therapeutically effective at low doses. The generally useful dose range is from about 0.001 mM, or less, to about 100 mM, or more. Preferably, the effective dose range is from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds will be generally administered in low doses.

The compound can be administered in a pharmaceutically acceptable carrier. Pharmaceutically acceptable carriers are well-known to those who are skilled in the art. The choice of carrier will be determined in part by the particular compound, as well as by the particular method used to administer the composition. Accordingly, there is a wide variety of suitable formulations of the pharmaceutical composition of the preferred embodiments.

The compounds can be administered orally, topically, parenterally, by inhalation or spray, vaginally, rectally or sublingually in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Compounds of the preferred embodiments can also be administered transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

Pharmaceutical compositions of the preferred embodiments can also be in the form of oil-in-water emulsions. The oil phase can be a vegetable oil, for example olive oil or arachis oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

For all regimens of use disclosed herein for active agent, the daily oral dosage regimen will preferably be from about 0.01 to about 200 mg/Kg of total body weight. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily dosage for administration by injection, including intravenous, intramuscular, subcutaneous and parenteral injections, and use of infusion techniques will preferably be from about 0.01 to about 200 mg/Kg of total body weight. Preferably, the daily dosage for administration by injection, including intravenous, intramuscular, subcutaneous and parenteral injections, and use of infusion techniques will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily vaginal dosage regime will preferably be from about 0.01 to about 200 mg/Kg of total body weight. The daily topical dosage regimen will preferably be from about 0.01 to about 200 mg administered between one to four times daily. The concentration for vaginal dosage and topical dosage will preferably be that required to maintain a daily dose is of from about 0.1 to about 200 mg/Kg. Preferably, the daily oral dosage regimen will preferably be from about 0.01, 0.05, 0.1, 0.5, 1, 2, 3, 4, or 5 to about 10, 50, 100, 110, 120, 130, 140, 150, 160, 170, 180, 190, or 200 mg/Kg of total body weight. The daily inhalation dosage regimen will preferably be from about 0.01 to about 10 mg/Kg of total body weight. Preferably, the daily inhalation dosage regimen will preferably be from about 0.01, 0.05, 0.1, or 0.5 to about 1, 2, 3, 4, 5, or 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the preferred embodiments. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses can be determined using the assays described herein. When one or more of these small molecules is to be administered to an animal (e.g., a human) in order to modulate expression or activity of a polypeptide or nucleic acid of the preferred embodiments, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The examples disclosed below illustrated preferred embodiments and are not intended to limit the scope. It is evident to those skilled in the art that modifications or variations can be made to the preferred embodiments described herein without departing from the teachings of the present invention.

EXAMPLES

Recombinant protein production. Recombinant Trio (residues 1225-1537) containing the N-terminal DH/PH module, Rac1, Cdc42 and the p21-binding domain (PBD) of PAK1 (residues 51-135) are expressed in E. coli BL21 (DE3) strain as N-terminal $His_6$-tagged fusion proteins by using the pET expression system (Novagen). Rac1, Cdc42, Intersectin, PAK1 (PBD) and WASP (PBD) are expressed in E. coli DH5α strain as GST fusions by using the pGEX-KG vector. The N-terminal tagged GST or $His_6$ fusion proteins are purified by glutathione- or $Ni^{2+}$-agarose affinity chromatography. GST-Rho GTPases on glutathione beads are eluted off bound guanine nucleotides or $Mg^{2+}$ by washing with a buffer containing 50 mM Trio-HCl, PH 7.6, 100 mM NaCl, 1 mM EDTA, and 1 mM DTT.

In vitro complex formation assay. About 0.5 μg of $His_6$-tagged Trio is incubated with 0.5 μg, EDTA-treated, GST-fused Cdc42 or Rac1 in a binding buffer containing 20 mM Tris-HCl, pH 7.6, 100 mM NaCl, 1 mM DTT, 1% bovine serum albumin, 1% Triton X-100, 1 mM $MgCl_2$ and 10 μl suspended glutathione-agarose beads. ~0.75 μg of GST-tagged Intersectin is incubated with nucleotide-free, $His_6$-tagged Cdc42 or Rac1 (0.25 μg) in the binding buffer with 10 μl suspended glutathione-agarose beads. After incubation at 4° C. for 30 min under constant agitation, the glutathione beads are washed twice with the binding buffer. The amount of $His_6$-tagged protein co-precipitated with the GST-fusion bound beads is detected by anti-His Western blotting.

In vitro guanine nucleotide exchange assay. For these, 200 nM Rac1 loaded with mant-GDP is incubated at 25° C. in an exchange buffer containing 100 mM NaCl, 5 mM $MgCl_2$, 50 mM Tris-HCl (pH 7.6), and 0.5 mM GTP in the absence or presence of 200 nM Trio. The mant-GDP fluorescence changes in the course of the exchange reactions are monitored with an excitation wavelength at 360 nm and the emission wavelength at 440 nm by a Cary Ellipse fluorescence spectrometer (Varian, Inc.).

Cell culture. NIH 3T3 fibroblasts are grown in Dulbeeco's modified Dagle's medium supplemented with 10% calf serum. RWPE-1 cells are obtained from the American Type culture collection (ATCC) and are grown in keratinocyte-Serum Free medium (GIBCO-BRL) supplemented with 5 ng/ml EGF and 0.05 mg/ml bovine pituitary extract. PC-3 cells are cultured in RPM1 1640 medium (Cellgro) supplemented with 10% FBS.

Endogenous Rho GTPase activity assay. GST- or $His_6$-PAK1 (PBD) and GST-WASP (PBD) are expressed in Escherichia coli and purified by glutathione- or $Ni^{2+}$-agarose affinity chromatography. Cells are grown in log phase in a 10 cm dish, and are starved in 0.5% serum medium or indicated otherwise for 24 hrs prior to lysis in a buffer containing 20 mM Tris-HCl (pH 7.6), 100 mM NaCl, 10 mM $MgCl_2$, 1% NP-40, 10% glycerol, and 1× proteases inhibitor cocktail (Roch). Lysates are clarified and the protein concentrations are normalized. The cell lysates containing equal amount of proteins are incubated with 10 μg GST- or $His_6$-fusion probes for 40 min at 4° C. under constant rotation. The beads are washed twice with the lysis buffer, and the bound-Rho GTPases are detected by anti-Rac1 (Upstate), or anti-Cdc42 (BD Transduction Laboratories) Western blotting. Quantification of the Western blots is carried out using a LAS-1000 luminescent image analyzer (Fujifilm medical system, USA, Inc.).

Immunofluorescence. After overnight serum starvation in the presence or absence of 100 μM 23766, NIH 3T3 cells grown on cover glasses are treated with 10 nM PDGF for zero, five or ten minutes. The cells are fixed with 3.7% formaldehyde in PBS for 15 min, and permeabilized with 0.1% Trion X-100 for 20 min. The cellular actin is stained with TRITC-labeled phalloidin (Sigma) at 10 μg/ml in PBS for 40 min at room temperature. The actin and cell morphological changes are visualized by fluorescence microscopy.

Cell growth assay. Wild type and RacL61- or various GEF-transfected NIH 3T3 cells are grown in 5% calf serum. The cells are split in duplicate in 6-well plates at $5\times10^4$ cells per well and are counted daily with a hemocytometer for 4 days.

The growth rate of the prostate PC-3 cells is measured by the CellTiter 96 AQueous assay (Promega). 1,500 cells/well in 200 μl of 5% FBS medium are plated in 96-well plates and are grown under normal conditions. Cultures are assayed in 0, 1, 2, 3, 4, or 5 days by the addition of 20 μl of the combined MTS/PMS solution followed by incubation for one hour at 37° C. Absorbency is measured at a wavelength of 490 nm on an automated microplate reader.

Anchorage independent growth. The prostate epithelia RWPE and PC-3 cells ($1.25 \times 10^3$ per well) are grown in 0.3% agarose in the absence or presence of different doses of Compound NCI23766 following a published protocol (Qiu et al., 1997, which is incorporated herein by reference in its entirety). The number of colonies formed in soft agar is counted after ten days.

Cell invasion assays. The cell invasion assays are performed using 6.4-mm Biocoat Matrigel invasion chambers with 8.0-micron pore size PET membrane (Becton-Dickinson) according to the manufactory instructions. Briefly, $5 \times 10^4$ cells are resuspended in 0.5 ml of serum free culture medium and added to the upper chamber. 10% fetal bovine serum in the culture medium is used as a chemo-attractant in the lower chamber. After the cells are incubated for overnight, the number of cell passed through the Matrigel is counted.

Results

Virtual Screening for Rac1-specific inhibitors. In the three-dimensional (3D) structure of Rac1-Tiam1 complex, $Trp^{56}$ of Rac1 is buried in a pocket formed by residues $His^{1178}$, $Ser1^{184}$, $Glu^{1183}$, and $Ile^{1197}$ of Tiam1 and $Lys^5$, $Val^7$, $Thr^{58}$, and $Ser^{71}$ of Rac1 (Worthylake et al., 2000, which is incorporated herein by reference in its entirety). To identify Rac1-specific inhibitors based on the structural features surrounding $Trp^{56}$, a potential inhibitor-binding pocket is created with residues of Rac1 within 6.5 angstroms of $Trp^{56}$ in the Rac1-Tiam1 monomer, including $Lys^5$, $Val^7$, $Trp^{56}$, and $Ser^{71}$. A 3D database search is performed to identify compounds whose conformations would fit the binding pocket. In order to take the flexibility of the compounds into consideration during the screening process, the program UNITY, whose Directed Tweak algorithm allows a rapid, conformationally flexible 3D search (Hurst, 1994, which is incorporated herein by reference in its entirety), is applied.

The small molecule hits yielded by the UNITY program are next docked into the predicted binding pocket of Rac1 containing $Trp^{56}$ by using the program FlexX, an energy minimization modeling software that can quickly and flexibly dock ligand to protein binding site (Rarey et al., 1996, which is incorporated herein by reference in its entirety). Following the docking procedures, the compounds are ranked based on their predicted ability to bind the binding pocket using the program Cscore. Cscore generates a relative, consensus score based on how well the individual scoring functions of the protein-ligand complex perform (Clark et al., 2002, which is incorporated herein by reference in its entirety).

Compound NCI23766 specifically inhibits Rac1-GEF interaction. Compounds from the virtual screening, including Compound NCI23766, were obtained from the National Cancer Institute-Research Samples and Services from Developmental Therapeutics Program (Bethesda, Md.). Also, Compound NCI23766 can be synthesized as set forth herein.

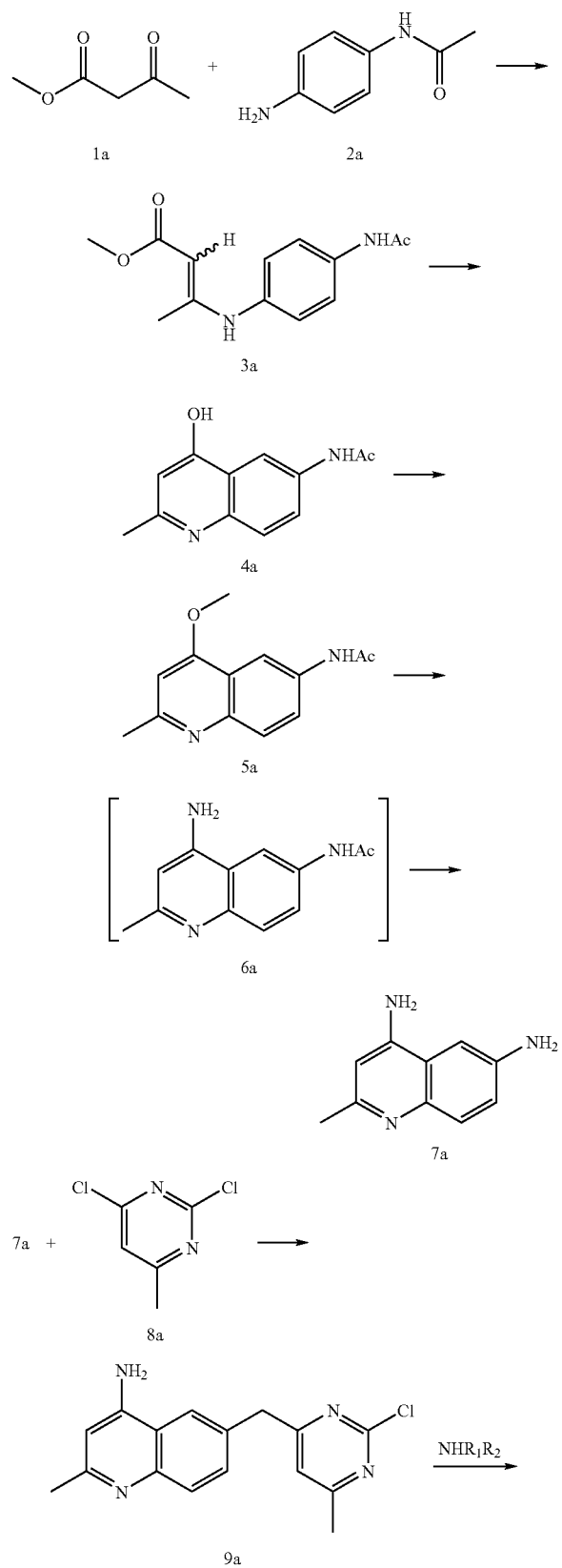

SYNTHETIC SCHEME 1

-continued

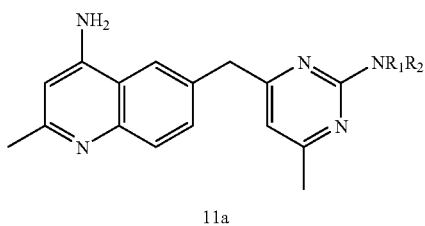

11a

Synthetic Scheme 1 follows closely the reaction conditions of Synthetic Scheme 2. In Synthetic Scheme 2, $NHR_1R_2$ is compound 10. $NHR_1R_2$ can be varied to be included within the preferred embodiments. $NHR_1R_2$ can be commercially available or synthesized using standard chemical methodologies. The reaction between $NHR_1R_2$ and Compound 9 or 9a is a standard amination reaction onto a haloaromatic ring.

The synthetic scheme described herein can be carried out using standard chemical methodologies described and referenced in standard textbooks. One may substitute other reagents known in the art which are known to be equivalent or perform a similar function. Starting material are commercially available reagents and reactions are preferably carried out in standard laboratory glassware under reaction conditions of standard temperature and pressure, except where otherwise indicated.

SYNTHETIC SCHEME 2

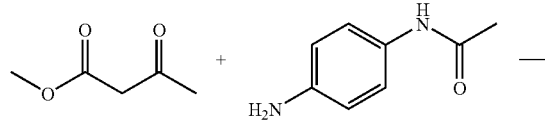

1        2

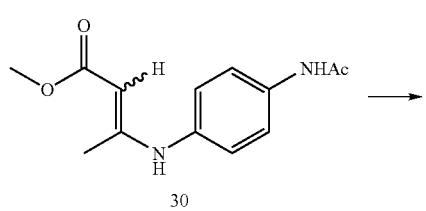

30

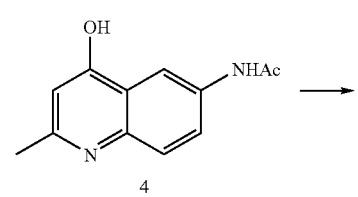

4

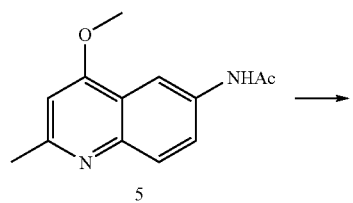

5

-continued

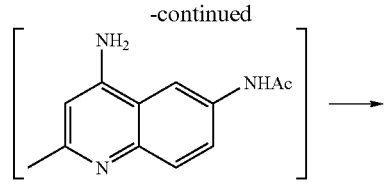

6

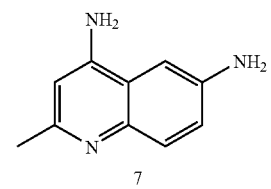

7

7 + 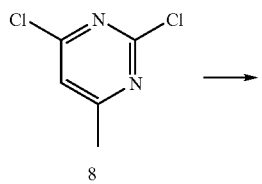

8

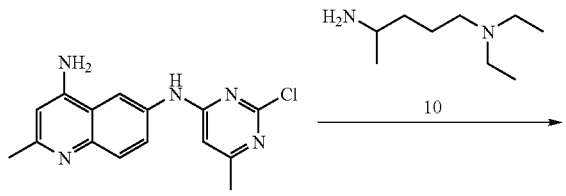

9

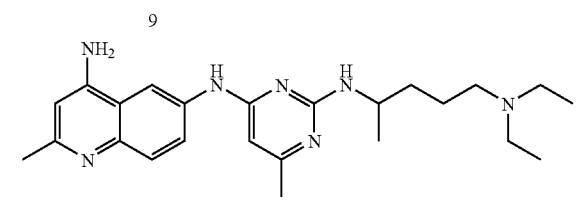

CHMC-1

EXPERIMENTAL

General

Raw materials were purchased from Aldrich, Acros, Fisher or Matrix Scientific. All solvents were ACS grade or better. Reactions were run under an atmosphere of dry nitrogen as necessary. Removal of solvents "in vacuo" refers to rotary evaporation using a Buchi apparatus at 25-50° C. and 45 Torr. Vacuum drying was done under high vacuum. All NMR spectra were recorded using a Varian-Gemini 300 spectrometer at 300 MHz for $^1$H NMR using $CHCl_3$ (7.26 ppm) or DMSO (2.5 ppm) as a reference and at 75 MHz for $^{13}$C NMR using $CDCl_3$ (77.0 ppm) or DMSO (39.43) as a reference.

Methyl 3-{[4-(acetylamino)phenyl]amino}but-2-enoate (3): A suspension of 4-aminoacetanilide (2) (253 g, 1.68 mol) and methyl acetoacetate (215 g, 1.85 mol) in MeOH (0.75 L) was heated to reflux. The resulting solution was held at reflux for 16 h and then cooled to 5° C. The resulting off-white precipitate was filtered and washed with MTBE (3×200 mL) to give butenoate 3 (195 g, 47% yield). The mother liquor was concentrated in vacuo and filtered to give a second crop of 3 as pale pink solids (141 g, 34% yield, 81% overall yield). $^1$H NMR (DMSO) δ 10.22 (s, 1H), 9.97 (s, 1H), 7.57 (d, 2H), 7.11 (d, 2H), 4.65 (s, 1H), 3.56 (s, 3H), 2.04 (s, 3H), 1.94 (s, 3H); $^{13}$C NMR (DMSO) δ 169.64, 168.07, 159.33, 136.48, 133.55, 124.52, 119.44, 84.47, 49.77, 23.81, 19.68.

N-(4-Hydroxy-2-methylquinolin-6-yl)acetamide (4): Phenyl ether (1 L) was heated to 255° C. Butenoate 3 (334 g, 1.35 mol) was carefully added portionwise while maintaining temperature 245-260° C. After the addition was complete, the yellow-orange suspension was held at 255° C. for an additional 15 min. The mixture was slowly cooled to 40° C., the solids were collected by filtration and washed with EtOAc (3×500 mL) followed by MeOH (3×500 mL) to give hydroxy quinoline 4 as yellow-orange solid (256 g, 88% yield); $^1$H NMR (DMSO) δ 11.52 (br, s, 1H), 10.07 (s, 1H), 8.24 (s, 1H), 7.82 (d, 1H), 7.42 (d, 1H), 5.84 (s, 1H), 2.31 (s, 3H), 2.05 (s, 1H).

N-(4-Methoxy-2-methylquinolin-6-yl)acetamide (5): Dimethyl sulfate (294 g, 2.33 mol) was charged to a suspension of hydroxyquinoline 4 (287 g, 1.33 mol) in toluene (1.5 L) and the mixture was refluxed for 6 h. After cooling to ambient temperature, the resulting dark yellow solids were collected by filtration and washed with toluene. The dry solid was dissolved in water (2.5 L) and the pH adjusted to 14 using 35% aqueous NaOH (290 g). The resulting tan precipitate was collected by filtration, washed with copious amounts of water and dried in vacuo at 60° C. to give methoxyquinoline 5 as light tan solid (259 g, 85% yield); $^1$H NMR (DMSO) δ 10.18 (s, 1H), 8.46 (s, 1H), 7.76 (m, 2H), 6.84 (s 1H), 3.99 (s, 3H), 2.55 (s, 3H), 2.09 (s, 3H); $^{13}$C NMR (DMSO) δ 168.36, 160.99, 158.07, 144.86, 135.87, 128.27, 122.78, 119.26, 108.80, 101.20, 55.69, 25.08, 23.97.

2-Methylquinoline-4,6-diamine (7): Ammonium acetate (1.3 kg) was melted and methoxyquinoline 5 (256 g, 1.11 mol) was added. The dark solution was refluxed at 135 for 4 h. After LC/MS indicated conversion of 5 (M+1=231) to intermediate 6 (M+1=216), the reaction mixture was poured into 37% HCl (2.1 L) and water (800 mL). The mixture was refluxed for 10 h and then cooled to ambient temperature for overnight. LC/MS indicated conversion of all intermediate 6 to diaminoquinoline 7 (M+1=174). The mixture was cooled to 5° C. and the resulting dihydrochloride salt was collected by filtration. The salt was dissolved in water (1.5 L) at 75° C. Charcoal (13 g, Darco G-60, -100 mesh) was charged to the dark solution, the mixture was refluxed for 45 minutes and was filtered through Celite. The yellow filtrate was cooled and the pH adjusted to 14 using 35% aqueous NaOH (1 kg). The resulting precipitate was collected by filtration, washed with copious amounts of water and dried in vacuo at 60° C. to give diaminoquinoline 7 as off-white solid (136 g, 71% yield); $^1$H NMR (DMSO) δ 7.41 (m, 1H), 6.95 (m, 2H), 6.30 (s, 1H), 6.03 (br, s, 2H), 5.05 (br, s, 2H), 2.32 (s, 3H); $^{13}$C NMR (DMSO) δ 153.42, 149.46, 144.28, 142.09, 128.84, 120.59, 118.60, 102.15, 101.11, 24.42.

N-6-(2-chloro-6-methylpyrimidin-4-yl)-2-methylquinoline-4,6-diamine (9): Diaminoquinoline 7 (72.0 g, 0.416 mol) and 2,4-dichloro-6-methylpyrimidine (8) (67.8 g, 0.416 mol) were suspended in ethylene glycol (1 L). Addition of 37% HCl (35 mL, 0.43 mol) resulted in a yellow solution which was heated to and held at 50° C. for 4.5 h. The mixture was diluted with chilled water (1 L) which resulted in a thick white paste-like precipitate and the mixture was filtered through Celite. The Celite and solid containing the product and bis-substituted by-product was slurried in water (4 L) and the Celite and insoluble by-product were removed by filtration. The filtrate pH was adjusted to 14 using 1N aqueous NaOH (1 L) resulting in precipitation of product which was removed by filtration. The damp product was transferred to a rotovap flask and dried in vacuo by azeotropic water removal with toluene (3×1.5 L). Product 9 was obtained as an off-white solid (33.4 g, 27% yield; Notebook reference A134-137). Another batch of 9 (7.4 g, 17% yield; Notebook reference A134-134) was similarly obtained by reaction of 7 (25.0 g, 0.144 mol) and recovery as above; MS [M+1]=300, 302; $^{13}$C NMR (DMSO) δ 167.51, 162.58, 159.22, 157.61, 151.05, 145.99, 133.17, 128.96, 125.39, 117.38, 114.23, 102.45, 102.26, 24.68, 23.19.

CHMC-1: A suspension of intermediate 9 (32.7 g, 0.109 mol) and diisopropylethylamine (20.0 mL, 0.115 mol) in ethylene glycol (500 mL) was heated to 90° C. to give a golden solution. 2-Amino-5-diethylaminopentane (32.0 mL, 0.165 mol) was added and the mixture was heated to and held at 110° C. for 5.5 h. The mixture was cooled to room temperature and EtoAc (750 mL) and 1N aqueous NaOH (500 mL) were added resulting in a thick white paste-like precipitate. The solid was removed by filtration through Celite and the filtrate layers were separated. The aqueous layer was twice basified using 1N NaOH (300 mL) and back-extracted using EtOAc (750 mL). The combined organic layers were washed with brine (3×750 mL), filtered through Celite and solvent removed in vacuo to give a brown oil (44 g). Heptane was added to the oil and allowed to sit for several days before decanting the solvent. The oil along with 12 g of crude oil from another batch were purified by silica gel (1.5 kg) flash column chromatography using EtOAc/MeOH/NEt$_3$ (7:3:0.5).

Chemical compounds are examined for their ability to inhibit the Rac1 binding interaction with GEF in a complex formation assay.

FIG. 1. shows identification of Compound NCI23766 as an inhibitor of Rac1-Trio interaction. In the upper panel of FIG. 1, the inhibitory effect of a panel of compounds predicted by Virtual Screening on Rac1 interaction with TrioN was tested in a complex formation assay. 0.5 μg of (His)$_6$-tagged TrioN was incubated with GST alone or nucleotide-free GST-Rac1 (2 μg) in the presence or absence of 1 mM indicated NCI compound and 10 μl suspended glutathione-agarose beads. After an incubation at 4° C. for minutes, the beads associated (His)$_6$-TrioN were detected by anti-His Western blotting. In the lower panel of FIG. 1, the effect of the compounds on Cdc42 binding to Intersectin was determined similarly. ~1 μg of GST or GST-tagged Intersectin was incubated with the nucleotide-free (His)$_6$-tagged Cdc42 (0.25 μg) under similar conditions. Data are representative of the results from four independent experiments.

For this purpose, Trio and Tiam-1, which specifically activate Rac1 but not Cdc42 (Gao et al., 2001, which is incorporated herein by reference in its entirety) and Intersectin, a Cdc42-specific GEF (Karnoub et al., 2001, which is incorporated herein by reference in its entirety), are used to assay the binding activity to their respective substrates in the presence of 1 mM of each individual compound. Trio and Tiam-1 co-precipitate with GST-Rac1, but not GST or GST-Cdc42. The inhibitory effect of Compound NCI23766 appears to be specific towards the interaction between Rac1 and its GEFs since it does not interfere with the Cdc42 binding to Intersectin nor RhoA binding to PDZ-RhoGEF (FIG. 1). Further, the inhibitory effect of Compound NCI23766 on Rac1 is dose dependent (FIG. 2).

Figure 2A:
Figure 2A:
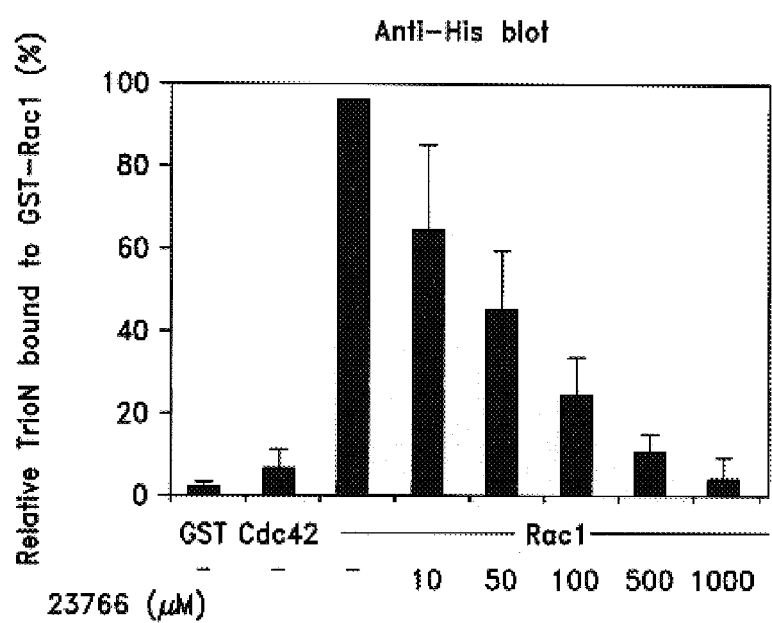

FIG. 2. shows dose dependent specific inhibition of GEF interaction with Rac1 by Compound NCI23766. In FIG. 2A, 0.5 μg of (His)$_6$-tagged TrioN was incubated with GST alone or nucleotide-free, GST-fused Cdc42 or Rac1 (2 μg) in the binding buffer containing different concentrations of Compound NCI23766 and 10 μl suspended glutathione-agarose. After an incubation at 4° C. for 30 minutes, the beads associated (His)$_6$-TrioN were detected by anti-His Western blotting. The blots were quantified by densitometry analysis. The results are representative of three measurements. In FIG. 2B, myc-tagged Tiam1 expressed in Cos-7 cell lysates were incubated with $(His)_6$-Rac1 in the presence of increasing concentrations of Compound NCI23766. The association of Rac1 with Tiam1 was examined by anti-His blot after anti-myc immunoprecipitation. In FIG. 2C, the AU-tagged PDZ-RhoGEF was expressed in Cos-7 lysates and incubated with GST or GST-RhoA in the presence of varying concentrations of Compound NCI23766. The RhoA associated PDZ-RhoGEF was probed with anti-AU antibody after affinity precipitation by glutathione agarose beads. In FIG. 2D, $(His)_6$-Rac1 loaded with GTPγS was incubated with GST-BcrGAP or GST-PAK1 (PBD) in the presence or absence of 200 μM Compound NCI23766 and the interaction with GSTBcrGAP or GST-PAK1 was probed by anti-His blot after affinity precipitation by glutathione agarose beads.

Figure 3A:
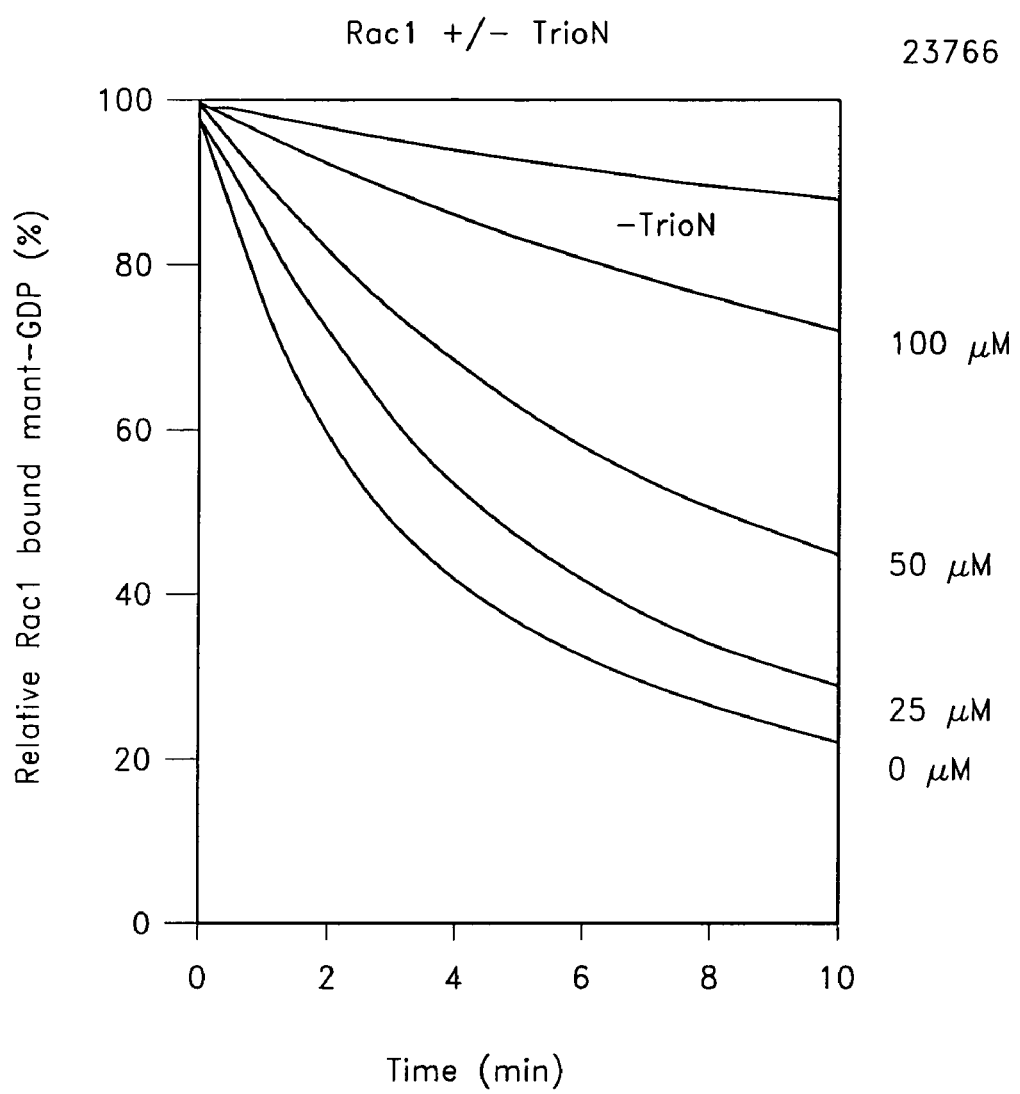
FIGS. 3A-3C show that Compound NCI23766 was effective in specifically inhibiting Rac1 GDP/GTP exchange stimulated by GEF.
Figure 3B:
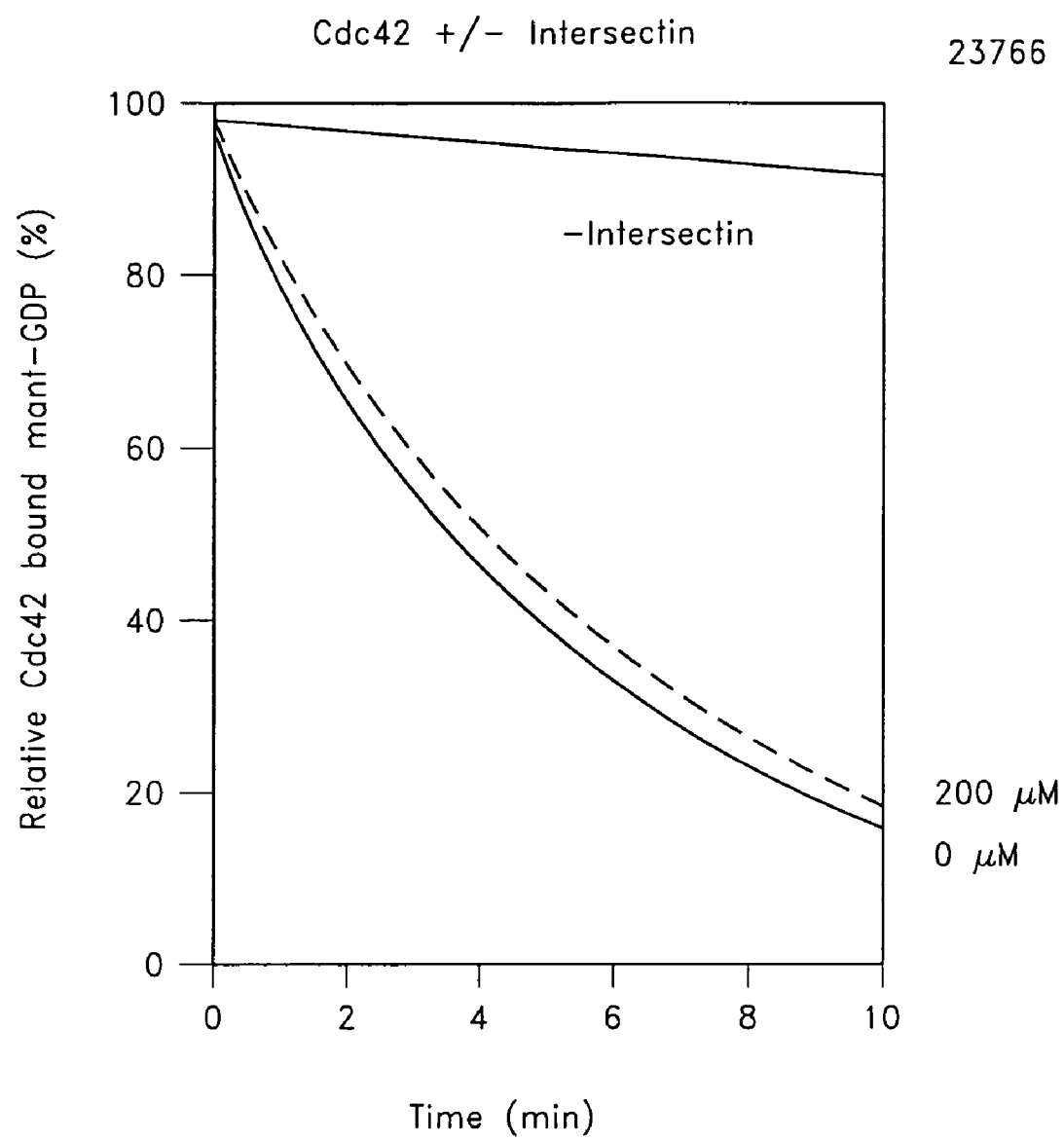
Figure 3C:
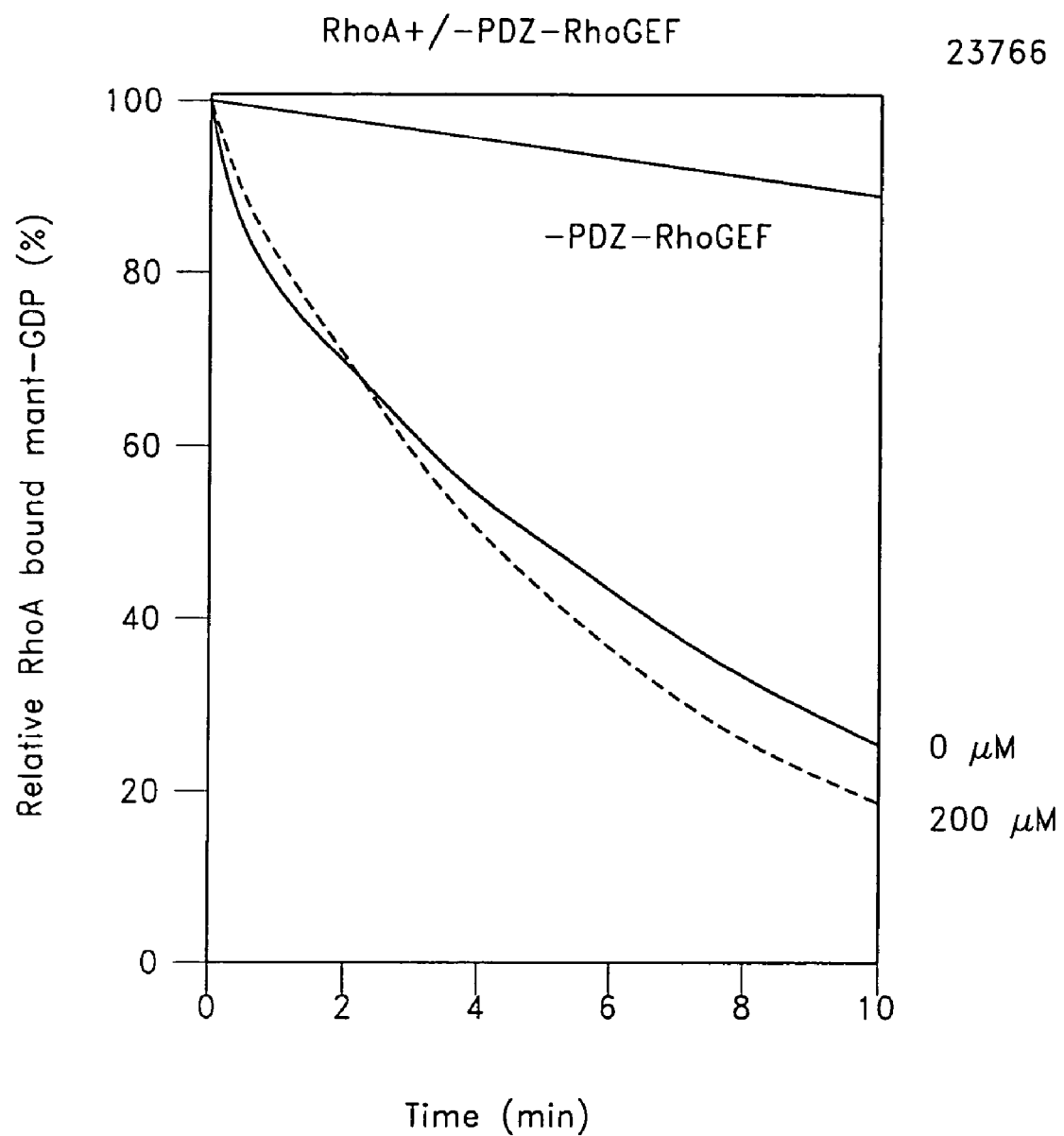

To determine if Compound NCI23766 is capable of inhibiting the GEF-stimulates nucleotide exchange of Rac1, the mantGDP dissociation assays of Rac1 are carried out in the presence of increasing doses of Compound NCI23766. In FIG. 3, Compound NCI23766 was effective in specifically inhibiting Rac1 GDP/GTP exchange stimulated by GEF. In FIG. 3A, Compound NCI23766 inhibited TrioN catalyzed GDP/GTP exchange of Rac1 in a dose dependent manner. 200 nM Rac1 loaded with mant-GDP was incubated at 25° C. in an exchange buffer containing 100 mM NaCl, 5 mM $MgCl_2$, 50 mM Tris-HCl (pH 7.6), and 0.5 mM GTP in the absence (top line) or presence of 100 nM TrioN. Increasing concentrations of Compound NCI23766 were included in the exchange buffer as indicated. In FIG. 3B, Compound NCI23766 had no effect on the Intersectin-stimulated GDP/GTP exchange of Cdc42. 200 nM Cdc42 loaded with mant-GDP was incubated in the exchange buffer in the absence (top line) or presence of 100 nM Intersectin with or without 200 μM Compound NCI23766. In FIG. 3C, the exchange reaction of RhoA catalyzed by PDZ-RhoGEF was carried out similarly in the presence or absence of 200 μM Compound NCI23766.

As shown in FIG. 3A, at increasing concentrations Compound NCI23766 is able to block the mantGDP/GTP exchange catalyzed by Trio in a dose-dependent manner. On the other hand, Compound NCI23766 has little impact on the Intersectin-stimulated mantGDP/GTP exchange of Cdc42 at similar doses (FIG. 3B), nor on the PDZ-RhoGEF-stimulated mantGDP/GTP exchange of RhoA. These results demonstrate that in vitro compounds, e.g., Compound NCI23766, are able to specifically inhibit the interaction and activation of Rac1 by its GEFs.

Figure 4A:
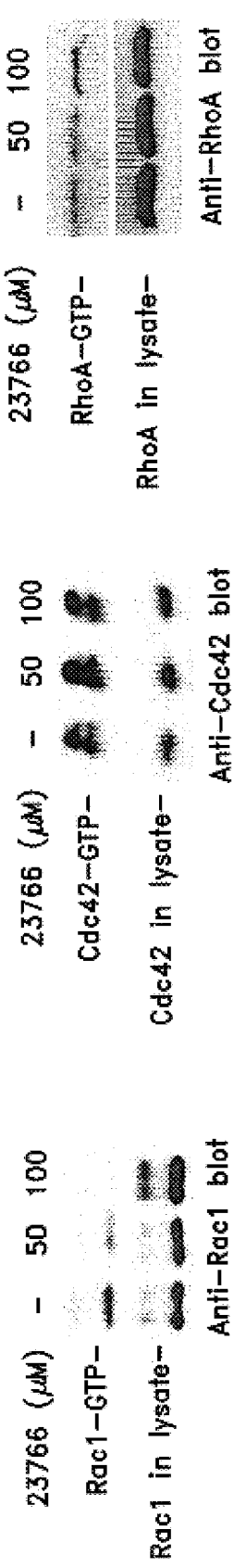
FIGS. 4A-4C show that Compound NCI23766 was effective in specifically inhibiting Rac1 activation in cells.
Figure 4B:
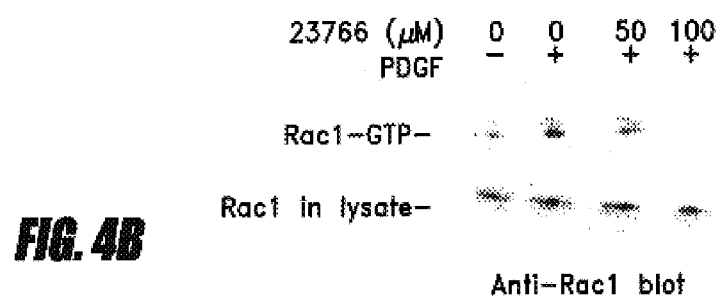
Figure 4C:
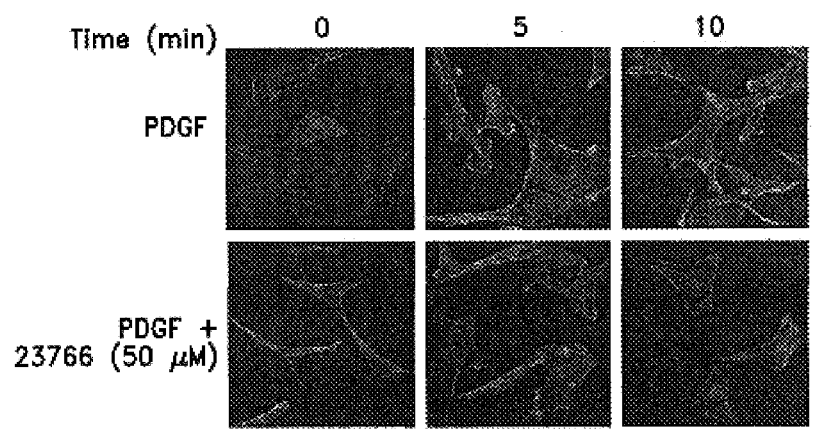

Inhibitory effect of Compound NCI23766 on Rac1 activity in vivo. In fibroblasts, Rac is activated by diverse stimuli including serum and PDGF (Hawkins et al., 1995, which is incorporated herein by reference in its entirety). Rac activation in these situations is expected to be mediated by one or more Rac-specific GEFs such as Tiam1. To evaluate how Compound NCI23766 can affect Rac activity in vivo, NIH 3T3 cells grown in 10% calf serum are treated with compound 23766 in different concentrations overnight, and the activation state of endogenous Rac1 in cells is detected by using the probe, GST-PAK (PBD) domain, that can specifically complex with Rac1-GTP. FIG. 4 shows that Compound NCI23766 was effective in specifically inhibiting Rac1 activation in cells. In FIG. 4A, the activation states of endogenous Rac1, Cdc42 and RhoA in NIH3T3 cells with or without Compound NCI23766 treatment were detected by the effector pull-down assays. At 80% confluency in the presence of 10% serum, NIH3T3 cells in 100 mm dishes were treated with the indicated dosages of Compound NCI23766 for 12 hours. Cell lysates containing similar amount of Rac1, Cdc42 or RhoA were incubated with the agarose immobilized GST-PAK1, GST-WASP or GST-Rhotekin, and the co-precipitates were subjected to anti-Rac1, Cdc42 or RhoA Western blot analysis to reveal the amount of GTP-Bound Rho proteins. In FIG. 4B, the inhibitory effect of Compound NCI23766 on the PDGF-stimulated Rac1 activation was determined by the GST-PAK1 pull-down assay. Serum starved NIH 3T3 cells in the DMEM medium with different dosages of Compound NCI23766 were treated with 10 nM PDGF for 2 minutes. In FIG. 4C, Compound NCI23766 inhibited PDGF-stimulated lamellipodia formation. After overnight serum starvation in the presence or absence of 50 μM Compound NCI23766, Swiss 3T3 cells were treated with 10 nM PDGF for the indicated time. The cells were fixed and stained with Rhodamine-labeled phalloidin.

As shown in FIG. 4A, Compound NCI23766 strongly inhibits Rac1 activation induced by serum. Densitometric analysis reveals that the $IC_{50}$ of Compound NCI23766 is about 40 μM under these conditions. Meanwhile, the inhibitory effect of Compound NCI23766 appears to be specific toward Rac among Rho GTPases, since the activation state of Cdc42 in these cells under serum-stimulation is unaffected by the presence of Compound NCI23766. Interestingly, treatment with this reagent leads to a slightly increased level of RhoA-GTP in cells, consistent with previous reports suggesting that Rac1 can counter-react with RhoA activity. To examine if Compound NCI23766 can affect Rac1 activation by PDGF stimulation, serum starved NIH 3T3 cells in the presence or absence of the compound are challenged with 10 nM PDGF for 2 minutes, and the cell lysates are assayed for the active Rac1-GTP species. Comparing with the PDGF-stimulated Rac activity in the absence of Compound NCI23766, the cells treated with 50 μM Compound NCI23766 displays a significantly reduction of GTP-bound Rac (FIG. 4B), and the presence of 100 μM 23766 lead to lower than basal level of Rac1-GTP in the cells. Thus, consistent with the in vitro Rac1-GEF interaction results, Compound NCI23766 is able to specifically inhibit Rac1 activity in vivo.

PDGF activates Rac and induces Rac-mediated membrane ruffles and lamellipodia in fibroblasts (Hawkins et al., 1995; Ridley et al., 1992, which are incorporated herein by reference in their entirety). To evaluate the ability of Compound NCI23766 to inhibit Rac1-mediated morphological changes, the actin cytoskeleton structures, induced by PDGF in the absence or presence of Compound NCI23766, was examined. As shown in FIG. 4C, 10 nM PDGF potently stimulates membrane ruffling and lamellipodial formation in Swiss3T3 cells. However, in the presence of 100 μM Compound NCI23766, PDGF is only marginally effective in inducing lamellipodia at the cell edges at 5 min and completely ineffective at 10 min when the control cells that are not treated with Compound NCI23766 displays significant lamellipodia structures. These results suggest that Compound NCI23766 is effective in inhibiting Rac-mediated actin reorganization.

Compound NCI23766 specifically inhibits serum- or Trio-induced cell growth. Rho GTPase activities are important in cell growth regulation. Overexpression of dominant-negative Rac slows cell growth (Zheng et al., 1995b, which is incorporated herein by reference in its entirety). Conversely, constitutively active Rac increases growth rate of fibroblasts (Khosravi-Far et al., 1995, which is incorporated herein by reference in its entirety). Since Compound NCI23766 is able to decrease Rac activity in NIH 3T3 cells, its effect on the growth properties of normal NIH 3T3 cells and the NIH 3T3 cells expressing constitutively active Rac1, L61Rac1 was examine.

FIG. 5. shows that Compound NCI23766 specifically inhibited Rac GEF stimulated cell growth and transformation. In FIG. 5A, wild type (WT) or L61Rac1 expressing NIH 3T3 cells were grown in 5% serum in the presence (- --) or absence (—) of 100 μM Compound NCI23766. The cells were split in triplicate in 6-well plates at a density of $5 \times 10^4$ cells per well. The GTP-bound L61Rac1 and endogenous Rac1 of the L61Rac1-expressing cells were probed by GST-PAK1 pull-down after 12 hour treatment with increasing concentrations of Compound NCI23766. In FIG. 5B, WT or the GEF (Tiam1, Lbc or Vav) expressing NIH 3T3 cells were grown in 5% serum in the presence (---) or absence (—) of 100 μM NSC23766, and the cell numbers were determined by daily cell counting. In FIG. 5C, GST, L61Rac1, or Tiam1 transfected cells were treated with 50 μM Compound NCI23766 every two days. The foci numbers of the respective cells were quantified 14 days after transfection. In FIG. 5D, a stable transfectant of Tiam1-expressing NIH 3T3 cells was cultured in 0.3% soft-agar medium for 14 days in the presence or absence of 100 μM NSC23766. The number and the morphology of the colonies were examined under a microscope.

Figure 5A:
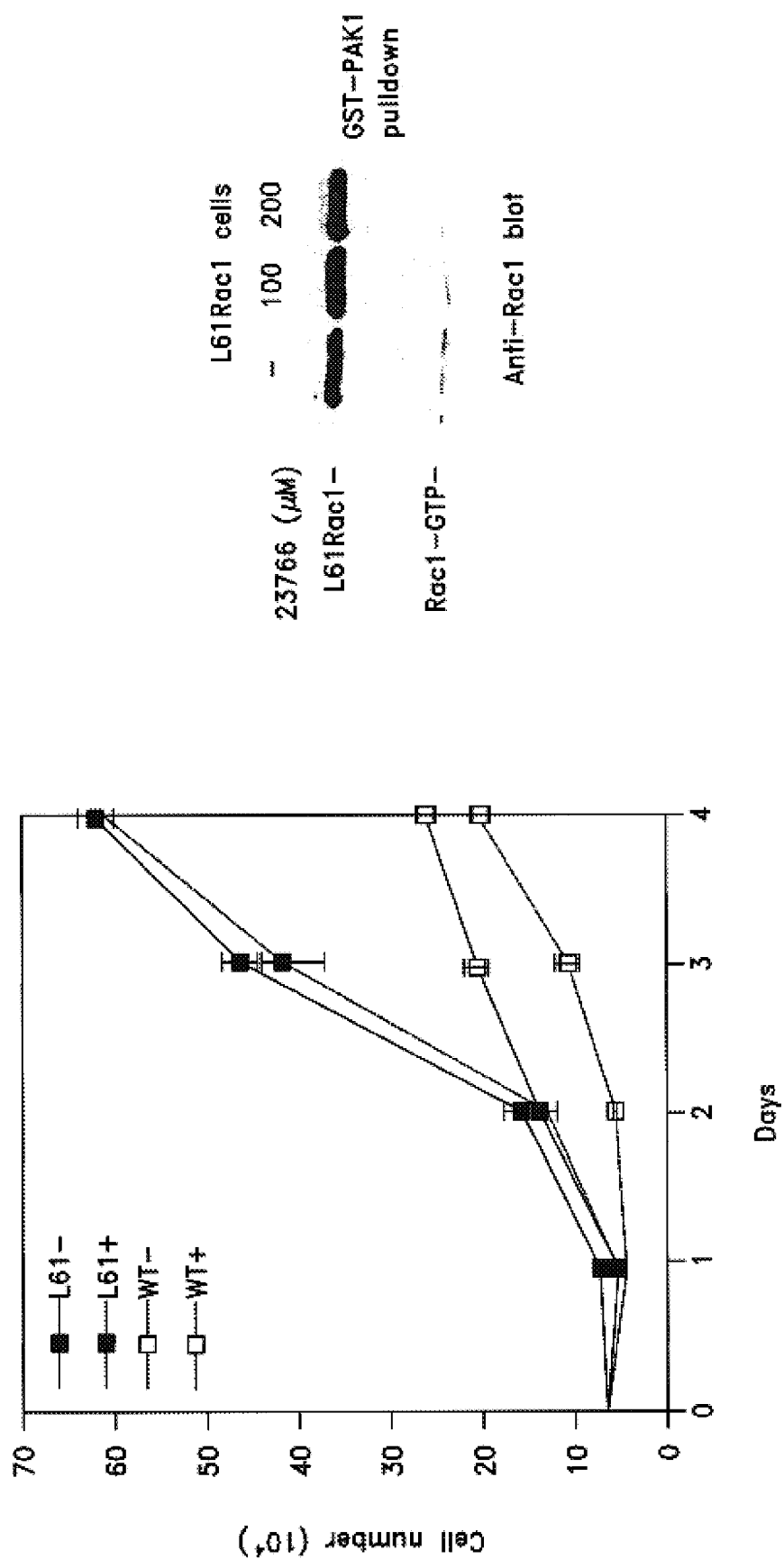
FIGS. 5A-5D show that Compound NCI23766 specifically inhibited Rac GEF stimulated cell growth and transformation.

Comparison of the growth rates of the cells in the absence or presence of Compound NCI23766 shows that Compound NCI23766 slow the growth of wild type NIH 3T3 cells while having no effect on the growth rate of Rac1L61 expressing cells (FIG. 5A). The level of GTP-bound GST-Rac1L61 remains unchanged with or without the compound treatment, whereas the endogenous Rac activity is deceased significantly by the presence of Compound NCI23766 (data not shown). These results suggest that the inhibitory effect of Compound NCI23766 on cell growth correlates with its ability to inhibit cellular Rac activity.

Figure 5B:
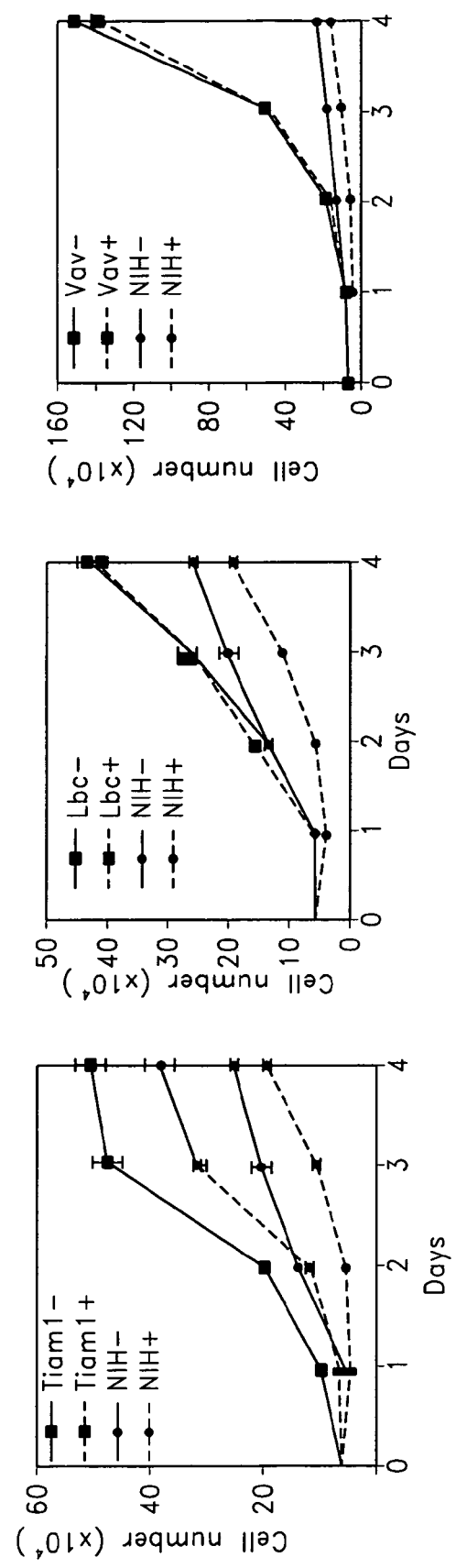
Figure 5C:
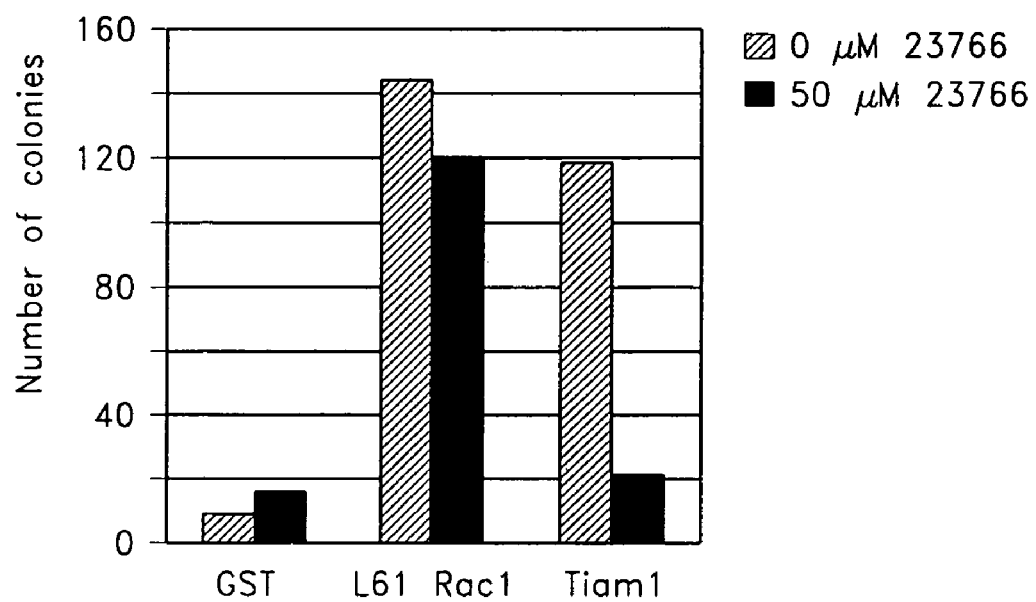
Figure 5D:
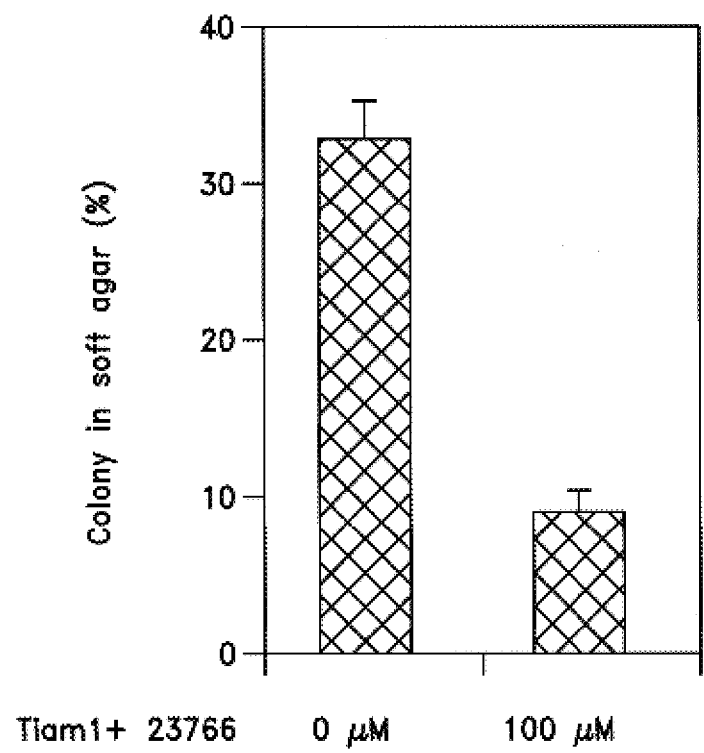
Figure 5D:
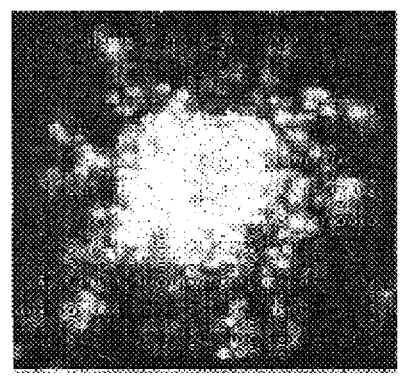
Figure 5D:
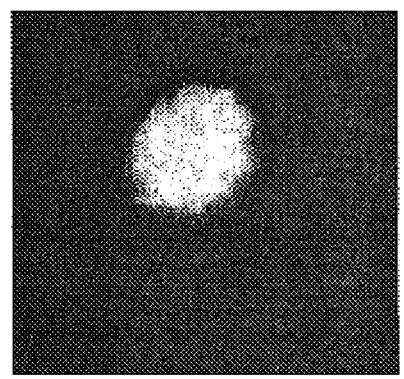

Due to their ability to directly activate Rho GTPases, Db1 family GEFs are potent stimulators of cell proliferation. Compound NCI23766 is capable of inhibiting the cell growth induced by the Rac specific GEF Trio, but not that stimulated by the Rho-specific GEF Lbc, the Cdc42-specific GEF Intersectin, or the multiple Rho protein-activating GEF Vav (FIG. 5B). Thus Compound NCI23766 is effective in specifically inhibiting cell growth caused by GEF-induced Rac activation.

Figure 6A:
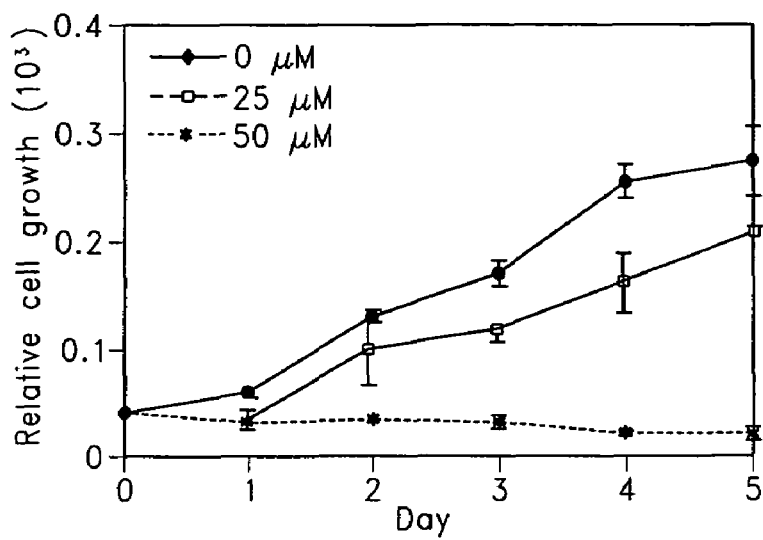
FIGS. 6A-6C show that Compound NCI23766 inhibited the proliferation, anchorage independent growth and invasion of PC-3 prostate cancer cells.

Reversal of the PC-3 tumor cell phenotypes by Compound NCI23766. Elevation of Rac1 activity is associated with cancer cell hyperproliferative and invasive properties. Next the effect of Compound NCI23766 is tested on the growth and invasion capabilities of a prostate cancer cell line, PC-3. PC-3 cells are malignant prostate adenocarcinoma cells derived from the bone metastases of a patient with prostate cancer (Kaighn et al., 1979, which is incorporated herein by reference in its entirety). They are transforming and highly invasive (Lang et al., 2002, which is incorporated herein by reference in its entirety). The mRNA of the PTEN tumor suppressor is undetectable in these cells (Bastola et al., 2002, which is incorporated herein by reference in its entirety), and loss of PTEN has previously been correlated with Rac1 hyperactivation due to the significant increase of $PIP_3$ level (Liliental et al., 2000, which is incorporated herein by reference in its entirety). When the activity of endogenous Rac1 in PC-3 cells is examined by probing with GST-PAK (PBD), a ~100% higher level of GTP-bound Rac than that of the normal prostate epithelial RWPE-1 cells is observed (FIG. 5A). Consistent with the results obtained from fibroblasts, Compound NCI23766 is able to inhibit Rac1 activity in PC-3 cells (FIG. 6A). Correlating with the decreased Rac1 activity, the proliferation rates of the Compound NCI23766 treated PC-3 cells are inhibited by Compound NCI23766 in a dose dependent manner (FIG. 6A). These results suggest that Compound NCI23766 can effectively inhibit PC-3 tumor cell growth through down-regulation of Rac1 activity.

FIG. 6. shows that Compound NCI23766 inhibited the proliferation, anchorage independent growth and invasion of PC-3 prostate cancer cells. In FIG. 6A, PC-3 cells were grown in 5% calf serum supplemented with the indicated concentrations of Compound NCI23766. The cells were split in triplicate in 96-wells at $1.5 \times 10_3$ cells per well. Cell numbers were assayed by using CellTiter 96 AQueous cell proliferation assay kit in different days. In FIG. 6B, PC-3 and RWPE-1 prostate epithelial cells ($1.25 \times 10_3$ per well) were grown in 0.3% agarose in different doses of Compound NCI23766, and the number of colonies formed in soft agar was quantified 12 days after plating. In FIG. 6C, PC-3 cells were placed in an invasion chamber for 24 hrs at 37° C. in the absence or presence of 25 μM Compound NCI23766. Cells invaded through Matrigel matrix were visualized with Giemasa staining.

Figure 6B:
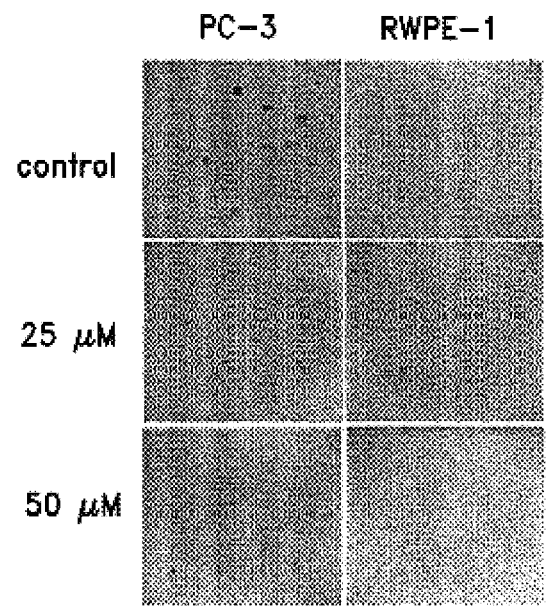
Figure 6B:
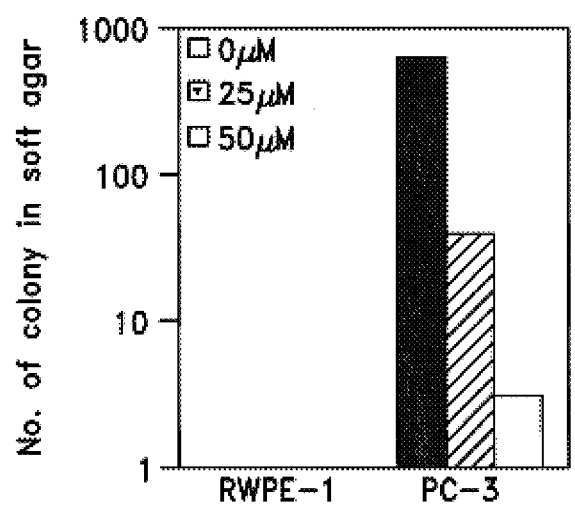
Figure 6C:
Figure 6C:
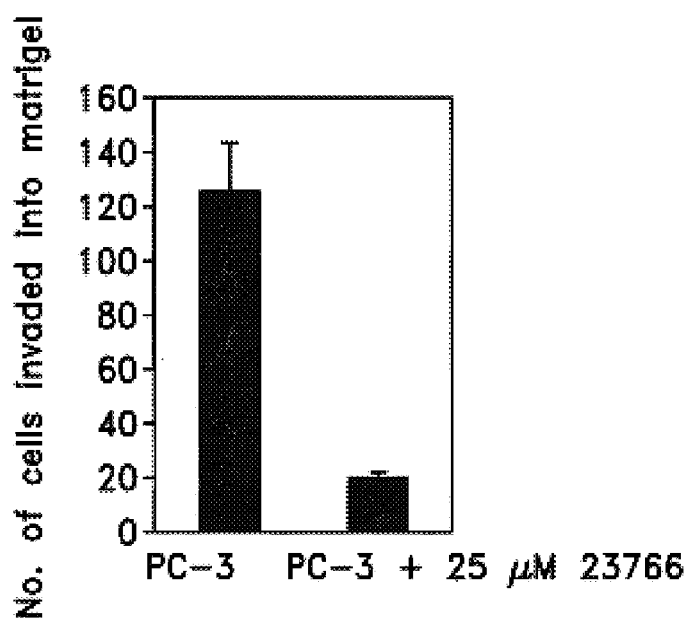

Given that PC-3 cells contain hyperactive Rac1 activity, the ability of PC-3 cells to grow on soft agar and the effect of Compound NCI23766 on its anchorage independent growth property can be tested. FIG. 6B shows that PC-3 cells readily form colonies ten days after being placed on soft agar, under conditions in which the normal prostate epithelia RWPE-1 cells are unable to grow. Compound NCI23766 efficiently blocks the colony forming activity of PC-3 cells. Approximately 10% and 1% colony-forming activities remain after treatment of the cells with 25 μM and 50 μM Compound NCI23766, respectively. Moreover, the size of colonies of the treated cells appears much smaller than those of the untreated ones (FIG. 6B). PC-3 cells are reported to possess highly invasive activity (Lang et al., 2002, which is incorporated herein by reference in its entirety), which is evident in a Matri-gel invasion assay. Under similar conditions, RWPE-1 cells are non-invasive. At a dose of 25 μM, Compound NCI23766 significantly inhibits PC-3 cell invasion (FIG. 6C).

Taken together, these results show that the active agent is able to downregulate Rac1 activity of PC-3 tumor cells which likely results in the reversal of the proliferation, anchorage independent growth and invasion phenotypes.

Controlling Platelet Hyperreactivity

In the studies disclosed hereinbelow, a dual approach of genetic targeting of Rac GTPases in mice and specific pharmacological inhibition of Rac GTPases in both mouse and human platelets was used to establish the central role of Rac GTPases in platelet function.

Genetic targeting of Rac GTPases—In experiments with gene targeted mice the following was observed: (a) platelets from Rac2−/− mice exhibit a 35% less adhesion to fibrinogen than platelets from WT mice; (b) ADP-, PLC- and collagen-induced fibrinogen binding to platelets from Rac2−/− mice, as compared to platelets from WT mice, was decreased by 65%, 40%, and 35%, respectively; (c) at threshold concentrations, thrombin, collagen, U46619, and PLC all elicited a slower onset of aggregation, as depicted by a prolonged shape change phase, in platelets from Rac2−/− than platelets from WT mice. Aggregation responses induced by thrombin, collagen, and U46619 were all diminished in platelets from Rac2−/− mice as compared to platelets from WT mice. Moreover, platelets from Rac2−/−, but not from WT, mice fail to exhibit irreversible aggregation even when challenged with higher concentrations of U46619 or collagen. Platelet aggregation responses induced by PLC and PMA, agents that bypass receptors, were also decreased in platelets from Rac2−/− mice than in platelets from WT mice.

Treatment of mice with Compound NCI23766, Formula IV. A specific small molecule inhibitor of Rac GTPase (Compound NCI23766; Formula IV) that acts on both Rac 1 and Rac 2 GTPases in a reversible fashion to effectively suppress cellular Rac activities and the intracellular signaling pathways regulated by Rac1 and Rac 2 was identified using a rationalized chemical library screening. This process was described above in the Experimental section of this document. Initial trials of this Rac inhibitor on platelet function investigated the effects of Compound NCI23766 on platelet adhesion, aggregation and secretion elicited by a variety of agonists. It was shown that Compound NCI23766 worked remarkably in inhibiting platelet adhesion, secretion, and aggregation induced by ADP, PLC, U46619, collagen, thrombin, or phorbol ester in a dose dependent manner. The inhibitory effect of Compound NCI23766 appears to be due to effective down regulation of Rac1/Rac2 activities and consequent inhibition of a Rac-regulated signaling cascade that may include the p21-activated kinase, myosin light chain kinase and p38 MAP kinase.

Taken together, these results show that Rac GTPases are involved in the regulation of platelet activation and can represent a convergent point for mediating multiple signaling pathways leading to platelet activation. Pharmacological blockade of Rac GTPase signaling by competitive inhibition of Rac activities by Compound NCI23766 or its derivatives, therefore, results in universal and reversible inhibition of platelet aggregation stimulated by multiple platelet activators.

In addition, information regarding procedural or other details supplementary to those set forth herein, are described in cited references specifically incorporated herein by reference.

It is be evident to those skilled in the art that modifications or variations can be made to the preferred embodiment described herein without departing from the novel teachings of the present invention. All such modifications and variations are intended to be incorporated herein and within the scope of the claims.

REFERENCES

Bastola, D. R., Pahwa, G. S., Lin, M. F., and Cheng, P. W. (2002). Downregulation of PTEN/MMAC/TEP1 expression in human prostate cancer cell line DU145 by growth stimuli. Mol. Cell Biochem. 236, 75-81.

Clark, R. D., Strizhev, A., Leonard, J. M., Blake, J. F., and Matthew, J. B. (2002). Consensus scoring for ligand/protein interactions. J. Mol. Graph. Model. 20, 281-295.

Del Pozo, M. A., Price, L. S., Alderson, N. B., Ren, X. D., and Schwartz, M. A. (2000). Adhesion to the extracellular matrix regulates the coupling of the small GTPase Rac to its effector PAK. EMBO J. 19, 2008-2014.

Engers, R., Zwaka, T. P., Gohr, L., Weber, A., Gerharz, C. D., and Gabbert, H. E. (2000). Tiam1 mutations in human renal-cell carcinomas. Int. J. Cancer 88, 369-376.

Etienne-Manneville, S. and Hall, A. (2002). Rho GTPases in cell biology. Nature 420, 629-635. Fritz, G., Just, I., and Kaina, B. (1999). Rho GTPases are over-expressed in human tumors. Int. J. Cancer 81, 682-687.

Gao, Y., Xing, J., Streuli, M. Leto, T. L., and Zheng, Y. (2001). Trp(56) of rac1 specifies interaction with a subset of guanine nucleotide exchange factors. J. Biol. Chem. 276, 47530-47541.

Gruneberg, S., Wendt, B., and Klebe, G. (2001). Subnanomolar Inhibitors from Computer Screening: A Model Study Using Human Carbonic Anhydrase II Agnew. Chem. Int. Ed Engl. 40, 389-393.

Guo, F., Gao, Y. Wang, L., and Zheng, Y. (2003). p19ARF-p53 tumor suppressor pathway regulates cell motility by suppression of PI3 kinase and Rac1 GTPase activities. J. Biol. Chem. paper in press.

Hawkins, P. T., Eguinoa, A., Qiu, R. G., Stokoe, D., Cooke, F. T., Walters, R., Wennsstrom, S., Claesson-Welsh, L., Evans, T., Symons, M., and Stephens, L. (1995). PDGF stimulates an increase in GTP-Rac via activation of phosphoinostitide 3-kinase. Curr. Biol. 5, 393-403.

Hurst, T. (1994). Flexible 3D searching: the directed tweak technique. J. Chem. Inf. Comput. Sci. 34, 190-196.

Kaighn, M. E., Narayan, K. S., Ohnuki, Y., Lechner, J. F., and Jones, L. W. (1979). Establishment and characterization of a human prostatic carcinoma cell line (PC-3). Invest Urol. 17, 16-23.

Kamai, T., Arai, K., Tsujii, T., Honda, M., and Yoshida, K. (2001). Overexpression of RhoA mRNA is associated with advanced stage in testicular germ cell tumour. BJU. Int. 87, 227-231.

Karnoub, A. E., Worthylake, D. K., Rossman, K. L., Pruitt, W. M., Campbell, S. L., Sondek, J., and Der, C. J. (2001). Molecular basis for Rac1 recognition by guanine nucleotide exchange factors. Nat. Struct. Biol. 8, 1037-1041.

Kato-Stankiewicz, J., Hakimi, I., Zhi, G., Zhang, J., Serebriiskii, I., Guo, L., Edamatsu, H., Koike, H., Menon, S., Eckl, R., Sakamuri, S., Lu, Y., Chen, Q., Agarwal, S., Baumbach, W. R., Golemis, E. A., Tamanoi, F. and Khazak, V. (2002). Inhibitors of Ras/Raf-1 interaction identified by two-hybrid screening revert Ras-dependent transformation phenotypes in human cancer cells. 99, 14398-13303.

Khosravi-Far, R., Solski, P. A., Clark, G. J., Kinch, M. S., and Der, C. J. (1995). Activation of Rac1, RhoA, and mitogen-activated protein kinases is required for Ras transformation. Mol. Cell Biol. 15, 6443-6453.

Lang, S. H., Hyde, C., Reid, I. N., Hitchcock, I. S., Hart, C. A., Bryden, A. A., Villette, J. M., Stower, M. J., and Maitland, N. J. (2002). Enhanced expression of vimentin in momtile prostate cell lines in poorly differentiated and metastatic prostate carcinoma. Prostate 52, 253-263.

Liliental, J., Moon, S. Y., Lesche, R., Mamillapalli, R., Li, D., Zheng, Y., Sun, H., and Wu, H. (2000). Genetic deletion of the Pten tumor suppressor gene promotes cell motility by activation of Rac1 and Cdc42 GTPases. Curr. Bio. 10, 401-404.

Mira, J. P., Bernard, V., Groffen, J., Sanders, L. C., and Knaus, U. G. (2000). Endogenous, Hyperactive Rac3 controls proliferation of breast cancer cells by a p21-activated kinase-dependent pathway. Proc. Natl. Acad. Sci. U. S. A 97, 185-189.

Movilla, N., Doseil, M., Zheng, Y., and Bustelo, X. R. (2001). How Vav proteins discriminate the GTPases Rac1 and RhoA from Cdc42. Oncogene 20, 8057-8065.

Perola, E., Xu, K., Kollmeyer, T. M., Kaufmann, S. H., Prendergast, F. G., and Pang, Y. P. (2000). Successful virtual screening of a chemical database for farnesyltransferase inhibitor leads. J. Med. Chem. 43, 401-408.

Qiu, R. G., Abo, A., McCormick, F., and Symons, M. (1997). Cdc42 regulates anchorage-independent growth and is necessary for Ras transformation. Mol. Cell Biol. 17, 3449-3458.

Rarey, M., Kramer, B., Lengauer, T., and Klebe, G. (1996). A fast flexible docking method using an incremental construction algorithm. J. Mol. Biol. 261, 470-489.

Ridley, A. J., Paterson, H. F., Johnston, C. L., Diekmann, D., and Hall, A. (1992). The small GTP-binding protein rac regulates growth factor-induced membrane ruffling. Cell 70, 401-410.

Sahai, E. (2002). Rho-GTPases and cancer. Nature Reviews Cancer 2, 133-142.

Schmidt, A. and Hall, A. (2002). Guanine nucleotide exchange factors for Rho GTPases: turning on the switch. Genes Dev. 16, 1587-1609.

Schmitz, A. A., Govek, E. E., Bottner, B., and Van Aelst, L. (2000). Rho GtPases: signaling, migration, and invasion. Exp. Cell Res. 261, 1-12.

Schnelzer, A., Prechtel, D., Knaus, U., Dehne, K., Gerhard, M., Graeff, H., Harbeck, N., Schmitt, M., and Lengyel, E. (2000). Rac1 in human breast cancer: overexpression, mutation analysis, and characterization of a new isoform, Rac1b. Oncogene 19, 3013-3020.

Stepan, V. M., Tatewaki, M., Matsushima, M., Dickinson, D. J., del Valle, J., and Todisco, A. (1999). Gastrin induces c-fos gene transcription via multiple signaling pathways. Am. J. Physiol 276, G415-G424.

Suwa, H., Ohshio, G., Imamura, T., Watanabe, G., Arii, S., Imamura, M., Narumiya, S., Hiai, H., and Fukumoto, M. (1998). Overexpression of the rhoC gene correlates with progression of ductal adenocarcinoma of the pancreas. Br. J. Cancer 77, 147-152.

Symons, M. (2000). Adhesion signaling: PAK meets Rac on solid ground. Curr. Biol. 10, R535-R537.

Van Aelst, L. and D'Souza-Schorey, C. (1997). Rho GTPases and signaling networks. Genes Dev. 11, 2295-2322.

Waszkowycz, B. (2001). Large-scale virtual screening for discovering leads in the postgenomic era. IBM systems J. 40, 360-376.

Worthlake, D. K., Rossman, K. L., and Sondek, J. (2000). Crystal structure of Rac1 in complex with the guanine nucleotide exchange region of Tiam1. Nature 408, 682-688.

Zhen, Y. (2001). Dbl family guanine nucleotide exchange factors. Trends Biochem. Sci. 26, 724-732.

Zheng, Y., Olson, M. F., Hall, A., Cerione, R. A., and Toksoz, D. (1995). Direct involvement of the small GTP-binding protein Rho in Ibc oncogene function. J. Biol. Chem. 270, 9031-9034.

Sorof, J., and Daniels, S. Obesity hypertension in children. A problem of epidemic proportions. Hypertension 40, 441-447 (2002)

Fitzgerald, D. J., Roy, L., Catella, F., Fitzgerald, G. A. Platelet activation in unstable coronary heart disease. N. Engl. J. Med. 315, 983-989 (1996)

Gawaz, M. Role of platelets in coronary thrombosis and reperfusion of ischemic myocardium. Cardiovas. Res. 61, 498-511 (2004)

Haszon, I., Papp, F., Kovacs, J., Bors, M., Nemeth, I., Bereczki, C., Turi, S. Platelet aggregation, blood viscosity and serum lipids in hypertensive and obese children. Eur. J. Pediatr. 162, 385-390 (2003)

Nityanard, S., Pande, I., Bajpai, V. K. Platelets in essential hypertension. Thromb. Res. 72, 447-454 (1993)

Blan, A. D., Lip, G. Y., Islim, I. F., Beevers, D. G. Platelet activation in hypertension. J. Hum. Hypertens. 11, 607-609 (1997)

Preston, R. A., Jy, W., Jimenez, J. J., Mauro, L. M., Horstman, L. L., Valle, M. Effects of severe hypertension on endothelial and platelet microparticles. Hypertension 41, 211-217 (2003)

Borijersen, A., Hamsten, A., Eriksson, M. Platelet activity in vivo in hyperlipoproteinemia-importance of combined hyperlipidemia. Thromb. Haemost. 79, 268-275 (2001)

Mandutaenu, I., Cal, M., Lupu, C. Increased adhesion of human diabetic platelets to cultured valvular endothelial cells. J. Submicrosc. Cytol. Pathol. 24, 539-547 (1995)

Tschoepe, D., Roesen, P., Schwippert, B., Gries, F. A., Platelets in diabetes: the role in hemostatic regulation in atherosclerosis. Semin. Thromb. Hemost. 19, 122-128 (1993)

Wincour, P. D. Platelet abnormalities in diabetes mellitus. Diabetes 41 (Suppl 2) 26-31 (1992)

Huo, Y. and Ley, K. F. Role of platelets in development of atherosclerosis. Trends Cardiovasc. Med. 14, 18-22 (2004)

Heeschen, C., Dimmeler, S., Hamm, C. W., van den Brand, M. J., Boersma, E., Zieher, A. M. Soluble CD40 ligand in acute coronary syndromes. N. Engl. J. Med. 348, 1104-1111 (2003)

Guyatt, G., Schunemann, H., Cook, D., Jaeschke, R., Pauker, S., Bulcher, H. Grades of recommendation for antithrombotic agents. Chest 119, 3S-7S (2001)

The SALT collaborative group. Swedish Aspirin Low Dose Trial of 75 mg aspirin as secondary prophylaxis after cerebrovasular ischemic events. Lancet 338, 1345-1349 (1991)

Serebruany, V. L., Murugesan, S. R., Pothula, A., Atar, D., Lowry, D. R., O'Connor, C. M., Gurbel, P. A. Increased soluble platelet/endothelial cellular adhesion molecule01 and osteonectin levels in patients with severe congestive heart failure. Independence of disease etiology, and antecedent aspirin therapy. Eur. J. Heart Failure 1, 243-249 (1999)

Roberts, A. W., et al. Immunity 10:183-196 (1999)

Gu, Y., et al. Science 302:445-449 (2003)

Huzoor-Akbar, Johnson, J. F., Williams, D. A., Zheng, Yi Rac2 GTPase plays a critical role in platelet adhesion as well as in sustenance and perpetuation of platelet aggregation. In preparation.

Gao, Y., Dickerson, J. B., Zheng, J., and Zheng, Y. (2004) Rational design and characterization of a Rac GTPase-specific small molecule inhibitor. Proc. Natl. Acad. Sci. U.S.A. 101, 7618-7623.

What is claimed is:

1. A method for treating platelet hyperreactivity in a subject, comprising administering to the subject in need thereof an effective amount of at least one compound having the formula (IIa):

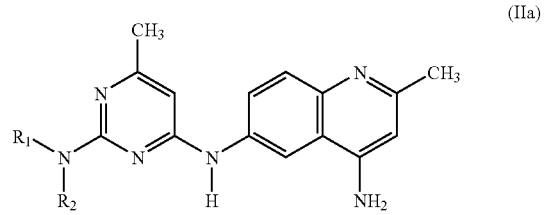

wherein:
$R_1$ to $R_2$ are independently selected from the group consisting of H, —X-Alk, —X-Alk-X', and —X—Y—X'; wherein
X is —$CR_7R_8$;
X' is —$CHR_7R_8$;
Alk is a $C_2$-$C_{18}$ substituted or unsubstituted hydrocarbon chain;
Y is a $C_2$-$C_8$ substituted or unsubstituted alkylene chain;
$R_6$ is H or ($C_1$-$C_4$) alkyl; and R₇ and R₈ are independently selected from the group consisting of H and (C1-C4) alkyl;

or a salt of a compound of formula (IIa), wherein the platelet hyperreactivity is a condition selected from the group consisting of arterial thrombosis, stroke, atherosclerosis, Kawasaki syndrome, and moyamoya.

2. The method of claim 1, wherein Alk is substituted with halo, halo (C1-C4) alkoxy, (C3-C8) cycloalkyl, hydroxy, or acetyl.

3. The method of claim 1, wherein Y is substituted with an NR₆ group.

4. A method for treating platelet hyperreactivity in a subject, comprising administering to the subject in need thereof an effective amount of at least one compound having the formula (III):

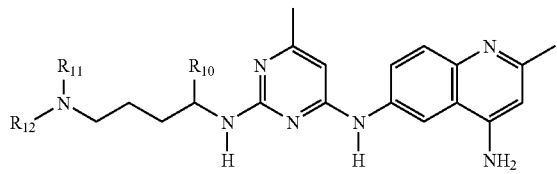

(III)

wherein:
R₁₀ to R₁₂ are independently selected from the group consisting of H, halo, (C1-C4) alkyl, branched (C3-C4) alkyl, halo (C1-C4) alkyl, (C1-C4) alkoxy, NO₂, and NH₂;

or a salt of a compound of formula (III), wherein the platelet hyperreactivity is a condition selected from the group consisting of arterial thrombosis, stroke, atherosclerosis, Kawasaki syndrome, and moyamoya.

5. The method of claim 4, wherein R₁₀ to R₁₂ are independently selected from the group consisting of H, (C1-C4) alkyl, and branched (C3-C4) alkyl.

6. A method for treating platelet hyperreactivity in a subject, comprising administering to the subject in need thereof an effective amount of at least one compound having the formula (IV):

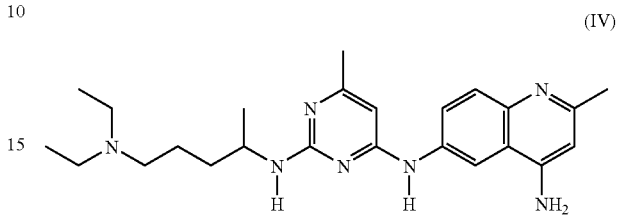

(IV)

or pharmaceutically acceptable salts thereof, wherein the platelet hyperreactivity is a condition selected from the group consisting of arterial thrombosis, stroke, atherosclerosis, Kawasaki syndrome, and moyamoya.

7. The method according to claim 1, wherein the compound is N6-(2-((4-(diethylamino) 1-methylbutyl)amino)-6-methyl-4-pyrimidinyl)-2-methyl-4,6-quinolinediamine.

8. The method according to claim 1, wherein the platelet hyperreactivity is mediated by a Rho GTPase selected from the group consisting of Rac1, Rac2, and combinations thereof.

9. The method according to claim 8, wherein the Rho GTPase is Rac1.

* * * * *

UNITED STATES PATENT AND TRADEMARK OFFICE
CERTIFICATE OF CORRECTION

PATENT NO. : 7,612,080 B2
APPLICATION NO. : 11/283556
DATED : November 3, 2009
INVENTOR(S) : Zheng et al.

It is certified that error appears in the above-identified patent and that said Letters Patent is hereby corrected as shown below:

On the first page, Item 56, Col. 2, line 2, under Other Publications, change "et al. ," to --et al.,--.

In Column 1, lines 20-21, change "The Government can have certain rights in this invention." to --The Government has certain rights in this invention--.

In Column 3, line 55, change "—NH (cycloalkyl)," to -- —NH(cycloalkyl),--.

In Column 4, line 53, change "4-piperidonyl," to --4-piperidinyl,--.

In Column 5, line 16, change "heterocylco," to --heterocyclo,--.

In Column 5, line 23, change "benzoxaxolyl," to --benzoxazolyl,--.

In Column 5, line 27, change "furopyridinyl," to --fluropyridinyl,--.

In Column 5, line 30, change "phenanthrollinyl," to --phenanthrolinyl,--.

In Column 6, line 19, change "RhoGTPases," to --Rho GTPases,--.

In Column 6, line 56, change "$R_6$" to --$R_9$--.

In Column 6, line 57, change "or" to --Or--.

In Column 7, line 22, change "RhoGTPases:" to --Rho GTPases:--.

In Column 7, line 63, change "or" to --Or--.

In Column 7, line 67, change "RhoGTPases:" to --Rho GTPases:--.

In Column 8, line 14, change "X'whereing" to --X', wherein--.

In Column 9, line 17, change "N6" to --N-6--.

In Column 9, line 29, change "$N^6$" to --N-6--.

In Column 9, line 35, change "$N^6$" to --N-6--.

In Column 9, line 51, change "N6" to --N-6--.

Signed and Sealed this

Twenty-second Day of June, 2010

David J. Kappos
*Director of the United States Patent and Trademark Office*

CERTIFICATE OF CORRECTION (continued)
U.S. Pat. No. 7,612,080 B2

In Column 10, line 47, change "RhoGTPases" to --Rho GTPases--.

In Column 11, line 34, change "RacGTPase," to -- Rac GTPase, --.

In Column 12, line 43, change "RacGTPase," to --Rac GTPase,--.

In Column 12, line 44, change "Rac 2," to --Rac2,--.

In Column 13, line 21, change "polymorphoneuclear" to --polymorphonuclear--.

In Column 13, lines 27-28, change "Imunopatholoy" to --Immunopathology--.

In Column 13, lines 43-44, change "myelo dysplastic" to --myelodysplastic--.

In Column 14, lines 2-3, change "spenomegaly," to --splenomegaly,--.

In Column 14, line 3, change "spenic" to --splenic--.

In Column 14, line 31, change "polyanglitis" to --polyangiitis--.

In Column 14, line 32, change "anglitis" to --angelitis--.

In Column 14, line 33, change "thromboanglitis" to --thromboangiitis--.

In Column 14, line 47, change "hemangloendothelioma," to --hemangioendothelioma,--.

In Column 14, line 48, change "hemangiopcricytoma;" to --hemangioperciytoma;--.

In Column 15, line 24, change "Szary" to --Sezary--.

In Column 15, line 62, change "insofar" to --in so far--.

In Column 18, line 44, change "undecanoates," to --undecenoates,--.

In Column 19, line 56, change "guandine" to --guanidine--.

In Column 19, line 61, change "fonic" to --folic--.

In Column 23, line 55, change "fumarate.Additional" to --fumarate. Additional--.

In Column 23, line 58, change "isosorbid" to --isosobide--.

In Column 23, line 64, change "discarboxylic" to --dicarboxylic--.

In Column 26, line 28, change "Dulbeeco's" to --Dulbecco's--.

In Column 26, line 29, change "Dagle's" to --Eagle's--.

In Column 31, line 26, change "(s 1H)," to --(s, 1H),--.

In Column 32, line 14, change "EtoAc" to --EtOAc--.

In Column 37, line 8, change "Rac 2" to --Rac2--.

In Column 38, lines 12-13, change "phosphoinostitide" to --phosphoinositide--.

In Column 38, line 41, change "momtile" to --motile--.

In Column 39, line 2, change "rac" to --Rac--.

In Column 39, line 11, change "GtPses:" to --GTPases:--.

In Column 39, line 25, change "rhoC" to --RhoC--.

In Column 39, line 47, change "(2002)" to --(2002).--.

In Column 39, line 50, change "(1996)" to --(1996).--.

In Column 39, line 53, change "(2004)" to --(2004).--.

In Column 39, line 57, change "(2003)" to --(2003).--.

In Column 39, line 60, change "(1993)" to --(1993).--.

In Column 39, line 63, change "(1997)" to --(1997).--.

In Column 40, line 3, change "(2001)" to --(2001).--.

In Column 40, line 6, change "(1995)" to --(1995).--.

In Column 40, line 9, change "(1993)" to --(1993).--.

In Column 40, line 11, change "(1992)" to --(1992).--.

In Column 40, line 13, change "(2004)" to --(2004).--.

In Column 40, line 17, change "(2003)" to --(2003).--.

In Column 40, line 20, change "(2001)" to --(2001).--.

In Column 40, line 23, change "(1991)" to --(1991).--.

In Column 40, line 30, change "(1999)" to --(1999).--.

In Column 40, line 31, change "(1999)" to --(1999).--.

In Column 40, line 32, change "(2003)" to --(2003).--.

In Column 42, line 26, in Claim 7, change "N6" to --N-6--.

UNITED STATES PATENT AND TRADEMARK OFFICE
CERTIFICATE OF CORRECTION

PATENT NO. : 7,612,080 B2 Page 1 of 1
APPLICATION NO. : 11/283556
DATED : November 3, 2009
INVENTOR(S) : Zheng et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 776 days.

Signed and Sealed this

Fifth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,612,080 B2  
APPLICATION NO. : 11/283556  
DATED : November 3, 2009  
INVENTOR(S) : Yi Zheng et al.

Page 1 of 1

It is certified that error appears in the above-identified patent and that said Letters Patent is hereby corrected as shown below:

Column 1, Line 18 through 21, delete from the specification of the above-identified patent:

"This invention was made in part with Government support under Grant No. R01 GM60523 and No. R01 GM53943 awarded by the National Institutes of Health. The Government has certain rights in this invention."

and <u>insert</u> therefore the following paragraph:

--This invention was made with government support under GM053943 and GM060523 awarded by the National Institutes of Health. The government has certain rights in the invention.--

Signed and Sealed this  
Twenty-third Day of September, 2014

Michelle K. Lee  
*Deputy Director of the United States Patent and Trademark Office*